(12) United States Patent
Oltra García et al.

(10) Patent No.: US 10,487,359 B2
(45) Date of Patent: Nov. 26, 2019

(54) METHOD FOR DIAGNOSING FIBROMYALGIA USING MICRORNAS

(71) Applicant: UNIVERSIDAD CATÓLICA DE VALENCIA "SAN VICENTE MÁRTIR", Valencia (ES)

(72) Inventors: Elisa Oltra García, Valencia (ES); Germán Cerdá Olmedo, Valencia (ES); Armando Vicente Mená Durán, Valencia (ES); María García Escudero, Valencia (ES); Vicente Juan Monsalve Dolz, Valencia (ES)

(73) Assignee: UNIVERSIDAD CATÓLICA DE VALENCIA "SAN VICENTE MÁRTIR", Valencia (ES)

( * ) Notice: Subject to any disclaimer, the term of this patent is extended or adjusted under 35 U.S.C. 154(b) by 0 days.

(21) Appl. No.: 15/501,097

(22) PCT Filed: Jul. 31, 2015

(86) PCT No.: PCT/ES2015/070599
§ 371 (c)(1),
(2) Date: Feb. 1, 2017

(87) PCT Pub. No.: WO2016/016507
PCT Pub. Date: Feb. 4, 2016

(65) Prior Publication Data
US 2018/0179592 A1    Jun. 28, 2018

(30) Foreign Application Priority Data
Aug. 1, 2014 (ES) .................................. 201431177

(51) Int. Cl.
| | | |
|---|---|---|
| C12N 15/11 | (2006.01) |
| C12Q 1/6876 | (2018.01) |
| A61K 31/7105 | (2006.01) |
| C12Q 1/68 | (2018.01) |
| C12Q 1/6837 | (2018.01) |
| C12Q 1/6883 | (2018.01) |

(52) U.S. Cl.
CPC ........ *C12Q 1/6876* (2013.01); *A61K 31/7105* (2013.01); *C12Q 1/68* (2013.01); *C12Q 1/6837* (2013.01); *C12Q 1/6883* (2013.01); C12Q 2600/158 (2013.01); C12Q 2600/178 (2013.01)

(58) Field of Classification Search
None
See application file for complete search history.

(56) References Cited

U.S. PATENT DOCUMENTS 8,173,611 B2    5/2012    Brown et al.

FOREIGN PATENT DOCUMENTS

| WO | 2012/048236 A1 | 4/2012 |
| WO | 2013/190091 A1 | 12/2013 |

OTHER PUBLICATIONS

He et al, A microRNA component of the p53 tumour suppressor network, Nature, 2007, 447: 1130-1134 (Year: 2007).*
Rivera J, González T: "The Fibromyalgia Impact Questionnaire: A validated Spanish version to assess the health status in women with fibromyalgia"; Clinical and Experimental Rheumatology (2004), 22, pp. 554-560.
Burckhardt CS et al: "The Fibromyalgia Impact Questionnaire: Development and Validation"; The Journal of Rheumatology (1991), 18(5), pp. 728-733.
Krupp et al.: "The fatigue severity scale, Application to Patients with Multiple Sclerosis and Systemic Lupus Erythematosus", Arch Neurol, (1989), 46(10), pp. 1121-1123.
Ware JE, Jr. et al.: "The MOS 36-item short-form health survey (SF-36), I. Conceptual Framework and Item Selection", Medocal Care (1992), 30(6), pp. 473-483.
Bullinger M et al: "SF-36 Health Survey in Rehabilitation Research. Findings from the North German Network for Rehabilitation Research, NVRF, within the rehabilitation research funding program"; Rehabilitation (Stuttg) (2003), (4), pp. 218-225.
Bjersing et al.: "Profile of Cerebrospinal microRNAs in Fibromyalgia", PLOS One (2013).
Ambros V. et al: "A uniform system for microRNA annotation"; RNA (2003), 9(3), pp. 277-279.
Mraz M et al.: "MicroRNA isolation and stability in stored RNA samples"; Biochemical and Biophysical Research Communications 390 (2009), pp. 1-4
Jung M et al.: "Robust microRNA Stability in Degraded RNA Preparations from Human Tissue and Cell Samples", Clinical Chemistry (2010), 56(6), pp. 998-1006.
Eikmans M et al.: "Blood cell mRNAs and microRNAs: optimized protocols for extraction and preservation"; Blood (2013), 121(11), pp. e81-e89.
Nilsen TW: "Splinted Ligation Method to Detect Small RNAs"; Cold Spring Harbor Protocols (2013), pp. 54-58.

(Continued)

*Primary Examiner* — Ekaterina Poliakova-Georgantas
(74) *Attorney, Agent, or Firm* — Merchant & Gould P.C.

(57) ABSTRACT

Method of diagnosing fibromyalgia based on microRNAs. The invention provides a method for the molecular diagnosis of fibromyalgia patients, based on the analysis of the possible alteration of the levels of specific microRNAs in peripheral blood mononuclear cells. The method comprises the analysis of the levels of the microRNAs miR-223, miR-451, miR-338, miR-143 and miR-145 and the diagnosis of fibromyalgia when at least one, or preferably several thereof have decreased levels with respect to a reference value, which preferably is the level of each microRNA in healthy individuals. Three additional microRNAs are also provided, miR-21, miR-1260b and miR-1908, which can be used as negative controls to confirm the diagnosis. The method facilitates an objective diagnosis of fibromyalgia based on molecular markers that are determined from a sample such as blood, which is easy to obtain and process.

14 Claims, 7 Drawing Sheets
(7 of 7 Drawing Sheet(s) Filed in Color)

Specification includes a Sequence Listing.

(56) References Cited

OTHER PUBLICATIONS

Rui Song et al: "In situ hybridization detection of microRNAs"; Methods Mol Biol. (2010), 629, pp. 287-294.
Bandyopadhyay S et al.: "TargetMiner: microRNA target prediction with systematic identification of tissue-specific negative examples"; Bioinformatics (2009) 25(20), pp. 2625-2631.
Krek A et al.: "Combinatorial microRNA target predictions"; Nature Genetics (2005) 37(5) pp. 495-500.
Coronello C et al.: "ComiR: Combinatorial microRNA target prediction tool"; Nucleic Acids Research (2013); 41(Web Server issue), pp. W159-W164.
Wolfe et al.: "The American College of Rheumatology 1990 Criteria for the Classification of Fibromyalgia, Report of the Multicenter Criteria Committee"; Arthritis and Rheumatism (1990), 33(2), pp. 160-172.
Cerda-Olmedo et al.: "Identification of a MicroRNA Signature for the Diagnosis of Fibromyalgia"; PLOS One (2015), 10(3), e0121903, pp. 1/14-14/14.
Mena-Duran A V et al: "Micro Expression Profile in Fibromyalgia patients: A Pilot Matched Case Control Study"; Annals of the Rheumatic Diseases (2013), 72, Suppl 3, p. 715.
Bjersing J. L. et al.: "Profile of Cerebrospinal microRNAs in Fibromyalgia"; PLOS One (2013), 8(10), e78762, pp. 1-6.
Lovendorf M.B. et al: "MicroRNA-223 and miR-143 are important systemic biomarkers for disease activity in psoriasis"; Journal of Dermatological Science, Netherlands (2014), 75(2), pp. 133-139.
Carlsen A L et al: "Circulating MicroRNA Expression Profiles Associated With Systemic Lupus Erythematosus"; Arthritis and Rheumatism (2013), 65(5), pp. 1324-1334.
International Search Report for PCT/ES2015/070599, dated Sep. 22, 2015.

* cited by examiner

METHOD FOR DIAGNOSING FIBROMYALGIA USING MICRORNAS

This application is a National Stage application of PCT/ES2015/070599, filed 31 Jul. 2015, which claims priority to Spanish Patent Application No. P201431177, filed 1 Aug. 2014, the contents of all of which are hereby incorporated by reference in their entireties.

FIELD OF THE INVENTION

The invention relates to the sector of diagnostic methods based on detection of levels of microRNAs. Specifically, the invention refers to a diagnostic method based on measuring the levels of the microRNAs miR-223, miR-451, miR-338, miR-143 and/or miR-145 for diagnosing the disease of fibromyalgia.

BACKGROUND OF THE INVENTION

Fibromyalgia is a disease characterized by generalized musculoskeletal pain, with excessive hypersensitivity at multiple predefined points, without demonstrable organic alterations.

At times fibromyalgia has been related to the Chronic Fatigue Syndrome, with which it shares some similarities. However, and in spite of the fact that at times patients who suffer from the one may also suffer from the other, these diseases are clearly differentiated by the World Health Organization classification of diseases.

The current fibromyalgia diagnosis [World Health Organization (WHO) code M79.0 in the International Classification of Diseases manual (ICD-10)] is based on a clinical examination of the following eight symptoms:
  Difficulty thinking clearly
  Throat irritation
  Hypersensitivity of the lymph nodes
  Muscular pain
  Joint pain
  Headache
  Sleep disturbance
  Discomfort for more than 24 hours after strenuous effort According to the criteria established by the American College of Rheumatology (ACR), a person suffers from fibromyalgia if they present with a history of generalized pain for a minimum of three months, as well as pain in 11 or more of the 18 specific areas of hypersensitive points (areas of the body that are painful when pressure is applied thereto).

In an attempt to standardize the physical examination performed by psychometric questionnaires are also used, which include:
  a) Fibromyalgia Impact Questionnaire (FIQ) (Rivera J, Gonzalez T, "The Fibromyalgia Impact Questionnaire: a validated Spanish version to assess the health status in women with fibromyalgia", Clin Exp Rheumatol., 2004 September-October, 2285):554-60; Burckhardt C S et al., "The fibromyalgia impact questionnaire: development and validation", J Rheumatol. 1991, 18(5):728-33).
  b) Multidimensional Fatigue Questionnaire (MFI) for the evaluation of fatigue according to the Fatigue Intensity Scale (FIS) designed by Krupp and Associates (Krupp et al., "The fatigue severity scale. Application to patients with multiple sclerosis and systemic lupus erythematosus", Arch Neurol. 1989; 46(10):1121-3).
  c) Health and well-being questionnaire (SF36) (Ware J E, Jr., Sherbourne C D, "The MOS 36-item short-form health survey (SF-36). I. Conceptual framework and item selection", Med Care 1992; 30:473-483; Bullinger M et al, "[SF-36 Health Survey in Rehabilitation Research. Findings from the North German Network for Rehabilitation Research, NVRF, within the rehabilitation research funding program]", Rehabilitation (Stuttg). 2003, 42(4):218-25).

The diagnostic methods most used today are based in large part on criteria with a significant subjective component, which often results in not having real certainty about whether or not a patient suffers from fibromyalgia. Moreover, not infrequently there are cases in which there are years of delay in diagnosing the disease, with the resultant detriment to the patient.

The lack of an objective diagnosis, along with a high and increasing number of persons affected (2-5% of the population), causes frequent socio-occupational problems.

With respect to other types of diagnostic methods for the disease of fibromyalgia, an attempt is been made to establish some molecular marker of the disease. Thus, a scientific publication in which a microRNA is proposed as fibromyalgia marker forms part of the prior art, specifically the miRNA-145 (Bjersing et al., "Profile of Cerebrospinal microRNAs in Fibromyalgia", PLOS One Oct. 25, 2013, DOI: 10.1371/journal.pone.0078762). Said analysis is carried out by extracting cerebrospinal fluid from the patient by lumbar puncture and analysis of the sample.

The microRNAs (miRNAs) are monocatenary RNA molecules, normally of about 20-25 nucleotides, which have the ability to regulate the expression of specific genes by means of their post-transcriptional silencing, as a result of the miRNA joining the messenger RNA in a region in which they are complementary, the pairing leading to the degradation of the messenger RNA. The microRNAs are coded in the genome and are initially formed, as is known, as pri-miRNA, which is a long molecule of bicatenary RNA with the ability to form hairpins by complementarity between internal regions of the molecule. The so-called precursor microRNA, pre-miRNA, is formed when the pri-miRNA is processed by the drosha enzyme, which cuts off or eliminates the bases of the hairpins, that is, the unpaired ends. The pre-miRNA is transported from the nucleus to the cytoplasm, where it is fragmented by the dicer enzyme, which cuts it to the final length of 20-25 nucleotides, after which the resulting duplex is separated, resulting in two monocatenary RNAs, one of which is the mature microRNA, which performs its silencing action integrated in the RISC complex.

The prefix "mir" followed by a hyphen and a number is often used to refer to microRNAs. It is common to differentiate the pre-miRNA from the mature form by capital letters, so that the abbreviation "mir-" corresponds to the pre-miRNA, while the abbreviation "miR-" indicates that a mature microRNA is referred to. An abbreviation making reference to the species is often used in the front; thus, for example "hsa" refers to human microRNAs, of *Homo sapiens*.

Letters (a, b, c . . . ) are also often found after the numbering, which indicate that two microRNAs have nearly identical sequences, differing only in one or two nucleotides. There are also microRNAs the abbreviation of which ends with indications such as "-5p" or "-3p", which distinguish the microRNAs that originate from opposite arms (from the end 5' or from the end 3) of the same pre-miRNA.

Although criteria have been established for identifying and naming miRNAs (Ambros V., Barte B., Barte D. P., Burge C. B., Carrington J. C., Chen X., Dreyfuss g., Eddy S. r., Griffiths-Jones S., Marshall M., Matzke M., Ruvkun G. Tuschl T., "A uniform system for microRNA annotation", RNA 2003 9(3):277-279), the names of the microRNAs can be modified with respect to those initially published as the relation between sequences becomes better understood. Thus, in the databases dedicated to microRNAs, the access number, which is unique for each microRNA, can be considered to be the stable unique identifier for an entry.

Research is being carried out on the usefulness of some miRNAs in diagnosing diseases, for differentiating different types of cancer, or even for acting on them. Thus, for example, the family of the international application published as WO2012048236 refers to the use of microRNAs as biomarkers for identifying family and non-family colorectal cancer, while the family of the application WO2013190091 refers to circulating microRNAs as markers for breast cancer. Moreover, the U.S. Pat. No. 8,173,611 refers to a method for reducing the proliferation of cancerous cells which comprises introducing into the cell a synthetic molecule of bicatenary RNA, in which one of the chains is identical to a mature microRNA selected from the group miR-16, miR-96, miR-101, miR-105, miR-124, miR-142, miR-147, miR-206 and miR-346, wherein the chain complementary to the mature microRNA contains a chemical modification that increases the activity of the active chain. In the case of fibromyalgia, the previously cited tests, performed in cerebrospinal fluid, involve an intent to evaluate possible usefulness of these molecules as markers of the disease.

Since the disease of fibromyalgia is a disease with a complex diagnosis, it would be very positive to find some safe method of objective diagnosis that would be easy to carry out and analyze, and which would facilitate confirmation of the final diagnosis. It would be especially interesting that the diagnosis were of the molecular type in order to avoid any type of external distortion. It would be particularly interesting if the analyzed sample were easily obtainable and easy to handle in clinical practice, as well as quick. The present invention resolves this problem.

SUMMARY OF THE INVENTION

The invention refers to a method for diagnosing whether an individual suffers from the disease of fibromyalgia, which comprises the steps of:
a) measuring the level of at least the miR-223 and miR-451 in a peripheral blood sample taken from the individual;
b) deciding that the patient suffers from disease of fibromyalgia if the level of at least one of the two analyzed miRNAs miR-223 and miR-451 has a value lower than a reference value.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
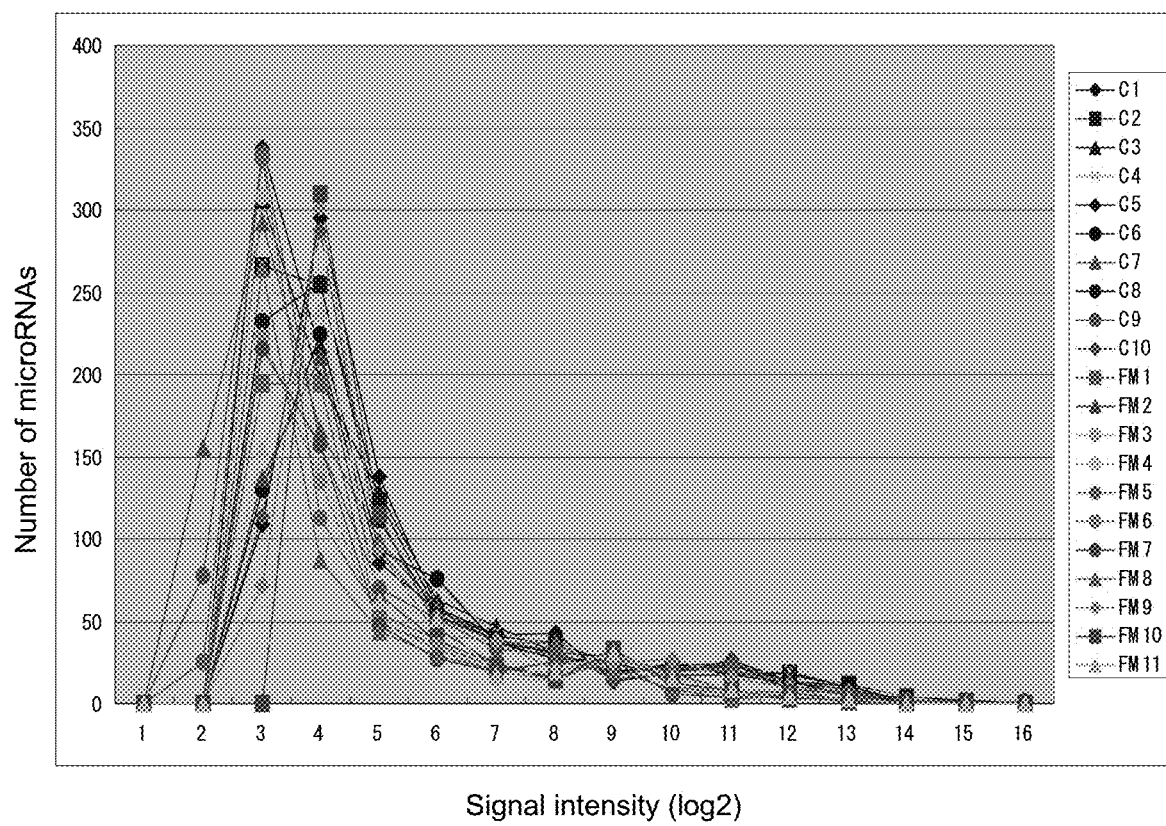
FIG. 1. Intensity histogram of the signals from the points of the microarray, after subtracting background noise (after standardization). Abscissa axis: intensity of the signal (base 2 logarithm of the detected signal); ordinate axis: number of microRNAs. The legend at the right indicates the relationship between the symbol of each curve and the sample to which it corresponds. Samples headed by the letter C correspond to controls, while those that begin with F correspond to fibromyalgia patients.

The object of the present invention relates to obtaining a molecular diagnostic method for the disease of fibromyalgia.

The invention is based on a study in which levels of expression were measured of a series of microRNAs (miRNAs) in peripheral blood samples, comparing the levels obtained in samples from healthy individuals with samples from individuals who suffer from the disease of fibromyalgia. The initial analysis was performed with techniques based on the hybridization of total RNA extracts obtained from peripheral blood mononuclear cells (PBMC) with complementary sequences present in microarrays, and on the comparison of the signals obtained for each microRNA between samples from fibromyalgia patients and healthy individuals (control subjects). The results showed a significant decrease in five specific microRNAs in fibromyalgia patients, results that were confirmed by quantitative PCR after reverse transcription.

In general, it was observed that in patients with fibromyalgia, the total quantity of miRNA is less than in healthy individuals, a marked predominance being detected of lower levels of miRNAs than those found in the control subjects. Thus, in order to make an accurate comparison, the comparison was made based on relative levels of miRNA. In this way, surprisingly, when the data were analyzed, it was observed that in the case of some miRNAs in particular, specifically the miRNAs miR-223, miR-451, miR-338, miR-143 and miR-145, the levels of expression of miRNAs in the patients are significantly reduced as compared to those of healthy individuals. Consequently, it being completely unexpected that specifically it would be this group of miRNAs that would have special relevance in diagnosing the disease of fibromyalgia and involving the miRNAs that had more accentuated differences in their levels of inhibition compared to the healthy controls, they are selected in order to establish an objective method of diagnosing said disease.

The diagnostic method of the invention comprises the measurement of the levels of at least one of the miRNAs of the group miR-223, miR-451, miR-338, miR-143 and miR-145, preferably from peripheral blood mononuclear cells (PBMCs) from the patient. Specifically, it is proposed to measure at least the miRNAs miR-223 and miR-451.

For the present invention microRNA (miRNA) of which the level is measured is understood as the corresponding mature miRNA. In fact, as discussed further hereinafter, the conditions of some of the assays described in the present application, such as quantification by qPCR, have been designed specifically to measure mature miRNAs, and not the possible pri-miRNA in all its forms and configurations and the pre-miRNA in all of its forms and configurations that may coexist in a same cell together with the corresponding miRNA, forming part of the same biological process.

Instead, the words microchip, microarray, oligoarray and oligochip are considered to be synonyms, and may be used interchangeably throughout the present invention. Microchip is understood as being a solid surface of small size, for example a slide, which acts as support to which an ordered collection of DNA or RNA fragments is attached, each of which is identified, knowing its nature and specific location in the microchip compared to the other members of the collection.

The method of the invention entails a clear advantage with respect to the prior art for various reasons. First, currently the most common way to diagnose the disease of fibromyalgia is by a physical examination performed by healthcare personnel in which it is determined if there is continuous pain at different specific points of the body. If there are a series of specific points of the body (specified in the background section of the invention) in which the patient is afflicted with pains as a consequence of a specific pressure, the patient is diagnosed with the disease of fibromyalgia. It is possible that the condition of the patient may vary from one examination to another, or may vary between patients due to different pain tolerance. Thus, for example a patient with a higher of pain tolerance could erroneously not be diagnosed with fibromyalgia, even though suffering therefrom. Instead, the method of the present invention facilitates the objective diagnosis of a chronic disease highly prevalent in developed countries (2.4% of the general population of more than 20 years of age), associated with disability.

Secondly, the study published in the journal PLOS ONE (Bjersing et al.), although it points out a possible biomarker of the disease, does not resolve the problem of easily and automatably diagnosing fibromyalgia in clinical practice. The tissue with which the analysis is carried out is cerebrospinal fluid, it being necessary to extract it first. Because of the prior extraction of said fluid, the patient must assume the risk of submitting to the procedure of lumbar puncture. Among other risks, the patient may suffer: bleeding in the spinal canal, discomfort during the examination, headache after the examination, hypersensitive reaction (allergic reaction) to the anesthesia, infection introduced by the needle when penetrating the skin, etc. Moreover, the location of the procedure must be a space duly prepared for that purpose, sterile and with the appropriate means and personnel for carrying it out with a minimum safety for the patient. Said means are much more difficult to obtain, primarily due to the cost thereof. The origin of the sample obtained in the present invention has many fewer complications than that of cerebrospinal fluid.

Lastly, the fact that the levels of miRNA vary in cerebrospinal fluid in patients suffering from fibromyalgia would not at all lead one to expect that in a completely different sample, like PBMCs, there could also be variations in some molecular marker that are related to the disease. As occurs with the level of gene expression, the levels of the miRNAs vary greatly from some tissues to others; it is very possible that the levels vary between tissues, without at all leading one to expect that said variation be maintained between tissues; it is also difficult to deduce which miRNAs can be altered in each tissue.

Until the present invention, there was no means of objectively diagnosing the disease of fibromyalgia, without risk and without generating that reasonable doubt resulting from the subjective testimony of the patient based on a physical clinical examination.

The present invention entails a solution for this lack of certainty in the most used current method, by being able to be used to confirm the diagnosis of the disease. Analysis of biological molecules is an easy method of standardizing since there is a measurement of the specific levels of expression of miRNA, which provides an empirical and objective component not influenced by the opinion of the patient at a specific time. Molecular diagnosis based on the measurement of the levels of a series of miRNAs offers the security and reliability lacking in the current diagnostic method. It is a method that can be reproduced under the same conditions with a high expectation that the results obtained, the interpretation thereof and the respective diagnosis hardly vary. It is a method completely independent of the opinion of the patient and of the circumstances that may be present at the time of the medical examination, increasing the degree of objectivity of the diagnosis.

Moreover, the concrete fact that the analyzed molecules are miRNAs is an advantage compared to other types of RNAs, since they have greater stability than the latter, which results in less risk of variability including in samples stored for different times after being obtained (Mraz M, Malinova K, Mayer J, Pospisilova S., "MicroRNA isolation and stability in stored RNA samples", Biochem Biophys Res Commun. 2009 Dec. 4; 390(1):1-4. doi:10.1016/j.bbrc.2009.09.061, Epub 2009 Sep. 19, Rev. PubMed PMID: 19769940; Jung M, Schaefer A, Steiner I, Kempkensteffen C, Stephan C, Erbersdobler A, Jung K., "Robust microRNA stability in degraded RNA preparations from human tissue and cell samples", Clin Chem. 2010 June; 56(6):998-1006. doi:10.1373/clinchem.2009.141580. Epub 2010 Apr. 8. PubMed PMID: 20378769).

Furthermore, the ease with which the sample can be obtained is also an important advantage of the invention. The extraction, storage and processing of blood from patients is a daily technique in a medical context. Thus, such simplicity with respect to obtaining, storing and processing the sample is also an advantage for the healthcare personnel as well as for the patient.

Another advantage of the invention is that, based on the results of the diagnostic method along with the medical examination, the diagnosed patient can be treated more appropriately based on the state of their health. Consequently, the increase in the certainty of the diagnosis very significantly decreases the risk of error in the clinical diagnosis and of not providing the most effective treatment to the patient.

Therefore, the invention refers to a method for diagnosing whether an individual suffers from the disease of fibromyalgia, which comprises the steps of:
a) measuring the level of at least the miR-223 and miR-451, miR-338, miR-143 and miR-145, in a peripheral blood sample taken from the individual;
b) deciding that the patient suffers from disease of fibromyalgia if the level of at least one of the analyzed miRNAs from the group miR-223, miR-451, miR-338, miR-143 and miR-145, has a value lower than a reference value.

In the method of the invention, it is proposed to measure at least two of the miRNAs from the aforementioned group in order to have a diagnosis of the disease of fibromyalgia. As can be seen in the results from the assays that are presented hereinafter in the Examples of the present application, each of the selected miRNAs independently makes it possible to diagnose those suffering from fibromyalgia However, the analysis of a single miRNA in PBMCs does not make it possible to diagnose all patients included in the present study. This is not surprising, since fibromyalgia is a disease with a variable clinical picture. Moreover, the patients included in the study on which the invention is based produced variable scores on forms used to verify its diagnosis (FIQ, MFI and SF-36, as is specified hereinafter). Thus, it is preferred that the method of diagnosing fibromyalgia of the present invention be based on the observation of the alteration of the levels of a group of miRNAs; preferred embodiments of the present invention are those in which the diagnosis is based on the analysis of the alteration of combinations (of at least two) of the miRNAs from the group of miR-223, miR-451, miR-338, miR-143 and miR-145.

In the present invention, it is preferred that at least one of the measured miRNAs be the miRNA-223 or miRNA-451, since as is observed hereinafter in Table 5, all patients who suffer from the disease show a decrease in the levels of expression of at least one of these two miRNAs. Therefore, when only one miRNA is measured, it would be most appropriate that said miRNA be one of the two that has the greatest decrease in patients in order to have greater certainty of the diagnosis. More preferably, both the miR-223 and miR-451 are measured, and if at least one of them is less than its corresponding reference value, it is determined that the patient has fibromyalgia. In addition, it is also preferred to measure the level of at least one, two or three miRNAs selected from the group of miR-338, miR-143 and miR-145.

In another preferred embodiment of the present invention, the measurement is made in at least 4 of the 5 miRNAs since, by measuring a greater number of miRNAs, confidence in the results obtained from the measurement is considerably increased, which is especially important in a disease like fibromyalgia with such complex and even heterogeneous symptomatology. In the previous case, in which 4 of the 5 miRNAs are measured, it is preferable that the miRNA not included in the measurement be the miR-143 or the miR-145.

In the particular case of the miRNAs miR-143 and miR-145, it should be pointed out that they belong to the same cluster and are therefore co-transcribed and regulated at the transcriptional level by the same factors. It is interesting, as is shown later in Tables 4 and 5 of the Examples, that the results obtained in the analysis of both are very similar. For this reason, in the event an analysis is not made of one of the miRNAs, it is preferred that it be one of the two aforementioned miRNAs, miR-143 or miR-145, since, knowing the levels of expression of one of them, it is relatively easy to estimate a similar variation for the other one.

In a yet more preferable embodiment of the invention, the levels are measured of the five proposed miRNAs in order to obtain results that ensure the maximum confidence and sensitivity for the diagnosis of the disease at fibromyalgia.

The decision about whether or not a patient suffers from the disease of fibromyalgia is preferably made based on various miRNAs showing a lower level than their respective reference value. In this way, as has been mentioned, in the present invention it is preferred that the level of at least two miRNAs be determined from the group miR-223, miR-451, miR-338, miR-143 and miR-145, particularly at least miR-223 and miR-451, and more preferably, at least four miRNAs; especially in the second case, it is preferred that it be established that a patient suffers from the disease of fibromyalgia if the level of at least two of the analyzed miRNAs has a value lower than its corresponding reference value. Particularly, at least one of the two analyzed miRNAs, miR-223 and miR-451, should have a value lower than a reference value, and in addition, at least one of the miRNAs from the group miR-338, miR-143 and mir-145 should have a value lower than a reference value. In an especially accurate analysis, it can also be established that a patient is considered to have fibromyalgia if the level of at least three or even four of the five miRNAs has a value lower than its corresponding reference value.

In order to establish a strict comparison between the relative levels of miRNAs measured from patients who suffer from fibromyalgia and the control subjects, it is essential to establish a reference value or control value with which to compare the levels of the miRNAs of the measured samples. As used in the present application, the terms reference value and control value are understood as being synonymous. Said control value can be obtained in various ways, for example from previous studies that can be a comparison of cases and controls. Preferably in the present invention the reference value is considered to be the average value of the levels of expression of said miRNA obtained in a statistical study in healthy individuals. Specifically, for the purposes of the present invention it is preferred that a miRNA is considered to have a value lower than the reference value when the value of its level of expression is one half or less of the average levels of expression in healthy individuals (see Tables 4 and 5 hereinafter).

Moreover, the determination of the average level of expression of each specific miRNA could be achieved using any known method available to a person skilled in the art, for example by calculating the arithmetic mean, although in the Examples of the present invention they have been calculated by comparison of averages of the valid duplicates obtained in reference to their average experimental value in a hybridization study with complementary probes that form part of a microarray.

In those cases in which the diagnostic method needs to be particularly accurate, it can also be established that an miRNA has a value lower than its reference value when its level of expression is at least four times below the reference value. Other values can also be chosen as reference value, such as for example the value of the 75th percentile of the levels of miRNAs from healthy individuals. These types of options can result in a more sure diagnosis of patients, but also can result in not diagnosing some individuals who suffer from fibromyalgia. It is also compatible with the present invention that the reference value be the level of some other molecule that is not necessarily one of the five analyzed miRNAs. All of these possibilities fall within the scope of the method of the present invention.

In addition, for better reliability it is preferred that the diagnostic test also include the levels of at least one of the miRNAs miR-21, miR-1260b and miR-1908, as negative control, verifying that said level is not less than its corresponding reference value. In an even more preferable situation, the levels are measured of at least two of the miRNAs hsa-miR-21, hsa-miR-1260b and hsa-miR-1908, thus increasing confidence even more in the results and their accuracy. In a situation of even greater preference, it is preferred to measure the levels of expression of the three miRNAs miR-21, miR-1260b and miR-1908, verifying that at least two of them do not have a value lower than the corresponding reference value, in order to ensure with greater certainty the reliability of the diagnostic method of the present invention. It is also compatible with the invention that the level be determined of the three miRNAs miR-21, miR-1260b and miR-1908 and it be established that none of the three should have a value lower than their corresponding reference value in order to establish that a patient suffers from fibromyalgia.

In preferred embodiments of the invention, the preferred criteria with respect to their corresponding reference value and the circumstances in which the level of an miRNA from the group miR-21, miR-1260b and miR-1908 is considered less than their reference value are the same as those already mentioned for the microRNAs from the group miR-223, miR-451, miR-338, miR-143 and miR-145, that is: the reference value will preferably be the average level of expression of said microRNA in healthy individuals and it will be considered that the microRNA has a value lower than said reference value when the value detected in a sample is at least two times less (one half or less) than its corresponding reference value. Thus, the level of expression is considered not to vary in said miRNAs when the decrease of the level is above half compared to the reference value of healthy patients.

The choice of said microRNAs as negative controls is due to the fact that the levels of expression of the miRNAs miR-1260b and miR-1908 do not show a variation less than the reference value when the levels of expression of the miRNAs of healthy individuals are compared with those of patients suffering from fibromyalgia (see Table 4 of the Examples); in the case of miR-21, the levels observed in patients are less than half of those observed in the controls when the assays are carried out with microarrays, but their decrease was not significant in the qPCR tests. Verifying that the levels of said microRNAs do not decrease in order to determine that a patient suffers from fibromyalgia is an important advantage, since it acts as a negative control of the diagnostic method of the invention, thus increasing the accuracy of the method. Preferably, the diagnostic method that includes the determination of said microRNAs should also include criteria that take into account the possible heterogeneity of fibromyalgia patients in the negative control of the assay as well. As can be seen in the Examples hereinafter, the miRNAs miR-1260b and miR-1908 involve more restrictive negative controls (overall they have less inhibition) than the miR-21; however, the inclusion of the miR-21 in the analysis facilitates ensuring the diagnosis of patients like those referred to hereinafter as "FM9", in whom the miR-1260b has a decrease in value of more than 2 (decreases more than half) compared to the values in healthy individuals, but the decrease of the microRNAs miR-1908 and miR-21 has a value of less than 2.

Therefore, to be sure that the patient suffers from fibromyalgia, it is preferred that the method according to the present invention be carried out so that fibromyalgia is diagnosed when the patient fulfils any of the possible aforementioned criteria concerning the measurement and variation of the five miRNAs of the group miR-223, miR-451, miR-338, miR-143 and miR-145, and preferably also at least one of the microRNAs of the group hsa-miR-21, hsa-miR-1260b and hsa-miR-1908 should not be less than its corresponding reference value, as discussed in the previous paragraph.

In a specific embodiment of the foregoing, for which there is special preference, the method of the present invention comprises:
 a) measuring the level of at least
  i) four microRNAs selected from the group of miR-223, miR-451, miR-338, miR-143 and miR-145, the microRNA preferably not being included in the miR-143 or miR-145 measurement,
  ii) the three microRNAs from the group miR-21, miR-1260b and miR-1908;
 b) deciding that the patient suffers from fibromyalgia if
  i) at least two of the analyzed microRNAs from the group miR-223, miR-451, miR-338, miR-143 and miR-145 have a value of less than their respective reference value, and
  ii) at least two of the analyzed microRNAs from the group miR-21, miR-1260b and miR-1908 do not have a value of less than their respective reference value.

With this additional embodiment of the method an additional negative control is introduced that makes it possible to ensure that the results obtained are reliable and that a suitable method has been carried out under good conditions.

In particular, as was mentioned previously, at least one of the two analyzed miRNAs, miR-223 and miR-451, should have a value lower than a reference value, and in addition, at least one of the miRNAs from the group miR-338, miR-143 and mir-145 should have a value lower than a reference value.

In the present invention, preference is given to measuring the levels of miRNAs from blood samples. Specifically, it is preferred to carry out the method of the invention in peripheral blood mononuclear cells, since they are relatively easy to isolate and analyze. The sample is easily extracted, which makes it especially appealing for clinical diagnosis in a reasonable time, and without causing too much discomfort to the patient. The methods of isolating PBMCs are well known by persons skilled in the art and are generally based on collecting the peripheral blood sample in a tube that contains an anticoagulant, such as heparin or EDTA salts, and separating by density gradient centrifugation the fraction corresponding to the red blood cells (lower part of the tube), the layer or ring of lymphocytes and platelets (intermediate whitish phase, also known as buffy coat) and the layer corresponding to the plasma (upper liquid phase), as described in Example 1 of the present invention.

The determination of the levels of each miRNA to be analyzed in the PBMCs can be done from total RNA isolated from said PBMC's, as in the Examples of the present application, or after carrying out an enrichment in microRNAs with any known techniques such as enrichment by purification of small RNAs from total RNA, by preferred union columns of small-size nucleic acids or other alternative methods, as indicated in the manuals for the products miRVana miRNA isolation kit (LifeTechnologies: https://www.lifetechnologies.com/order/catalog/product/AM1560), miRNEasy kit (Qiagen: http://www.qiagen.com/products/catalog/sample-technologies/rna-sample-technologies/mirna/mirneasy-mini-kit), u otros conocidos por los expertos en la técnica (Eikmans M, Rekers N V, Anholts J D, Heidt S, Claas F H, "Blood cell mRNAs and microRNAs: optimized protocols for extraction and preservation", Blood. 2013 Mar. 14; 121(11):e81-9. doi: 10.1182/blood-2012-06-438887. Epub 2013 Jan. 17. PubMed PMID: 23327925).

As mentioned hereinafter, the adaptation of traditional techniques, such as in situ hybridization, to the analysis of miRNAs also makes it unnecessary to isolate RNAs from the PBMCs in order to carry out the quantification of the miRNAs.

For detecting the level of the miRNA, any of the techniques known by a person skilled in the art can be used. For example, techniques can be used based on pairing of the miRNAs with complementary sequences and quantification of the miRNA associated with said sequences, or also through the use of quantitative polymerase chain reaction (qPCR) prior to conducting the reverse polymerase. In the first case, there are multiple well-known options, since the detection of the levels of miRNAs associated with their respective complementary sequences allows a multitude of variants, such as pairing with complementary sequences that form part of a microchip and detection and evaluation of the respective signal, preferably having previously labeled the miRNAs in the sample to be analyzed and detecting and quantifying the signal that is associated with a specific position of the microchip, which also makes it possible to identify said miRNA in a way similar to the test described in Example 1 of the present application. The labeling of the miRNA can be done in any manner known by a person skilled in the art, such as with radioactivity or a compound that emits florescence, as in the cited Example. As was mentioned previously, it is especially significant that, in the test described in Example 1 of the present application, the difference between the detected levels of the patients and of the healthy individuals (reference value) with the detection technique of miRNAs associated with their corresponding complementary sequence on a microchip is at least four times, and even six times, for any of the miRNAs of the group miR-223, miR-451, miR-338, miR-143 and miR-145.

Also compatible with the present invention is that it is the complementary sequence that is labeled by any known labeling method, as usually occurs when so-called "probes" are used (nucleic acid molecules with sequence complementary to at least one fragment of another nucleic acid which is to be detected) and the level of miRNAs is determined from the signal emitted by the complementary sequence that has remained attached thereto; normally, either the probe or the microRNAs present in the sample to be analyzed has previously been immobilized on a support, which can be of very diverse kind (polymer membranes such as nylon or nitrocellulose, polymers in the form of a multiwell plate, glass as in the case of conventional microchips, etc.), although the pairing between probe and microRNA can also be done in both forms in solution or suspension and removed from the unpaired hybrids or isolation of the probe-microRNA hybrids before proceeding with the detection and quantification of the signal.

Thus, in addition to microchips, any other technique can be used based on the association of the miRNAs with complementary sequences, for which there are many commercially available kits, protocols and specially designed equipment. Thus for example, SmartRNAplex® (MERCK) can be mentioned, based on particles that contain specific probes for specific miRNAs, and associated with a technique in which the determination of the levels of miRNAs is done in a flow cytometer.

Techniques for detecting alternative miRNAs such as the so-called "splinted ligation method" (Nilsen T W, "Splinted ligation method to detect small RNAs", Cold Spring Harb Protoc. 2013 Jan. 1; 2013(1), pii: pdb.prot072611, doi: 10.1101/pdb.prot072611.PubMed PMID:23282636), designed for the detection of small RNAs, which is based on joining the labeled 5' group of the RNA molecule to a DNA chain by means of the T4 ligase and a "splint" or oligonucleotide bridge complementary to the two, and in the subsequent detection of the labeled molecule after electrophoresis, as well as techniques similar to this one.

The detection and quantification of microRNAs can also be done by other traditional techniques that do not require their isolation from the sample in which they are present and in which they are to be detected, such as in situ hybridization (R, Ro S, Yan W., "In situ hybridization detection of microRNAs", Methods Mol Biol. 2010; 629:287-94, doi: 10.1007/978-1-60761-657-3_18, PubMed PMID: 20387156; PubMed Central PMCID: PMC3062509), immunodetection, or other similar techniques.

Another embodiment, which is included within the scope of the present invention like those previously mentioned, is the quantification of the levels of miRNAs measured by polymerase chain reaction (PCR), utilizing the variant known as quantitative PCR or real-time PCR (referred to in abbreviated form as qPCR, RT-PCR or qRT-PCR), which will preferably be performed after carrying out the reverse transcription of the RNAs (or at least of the microRNAs of interest) present in the sample to the analyzed. One possible specific embodiment, appropriate for the purposes of the present invention, is to carry out the qPCR on the cDNAs generated by reverse transcription using the oligonucleotides of Table 7 as forward primers, as in Example 2 the present application. Said forward primers have been specifically designed for the method of the present invention so that, among other advantages, a joint analysis can be carried out all of the miRNAs for the present invention and it is ensured that in each case the quantified miRNA is the mature miRNA. Alternatively, other forward primers can be used, which can be designed following specific criteria or selected from among commercially available primers such as, for example, those that are available for the miScript Primer Assays for the quantification of miRNA utilizing the miScript PCR System of Qiagen (http://www.qiagen.com/products/catalog/assay-technologies/mirna/miscript-primer-assays), which facilitates its combination with the same universal reverse primer used in the assays of the present application, also provided by Qiagen.

The pPCR technique can be used independently or also with the objective of verifying and ensuring the levels of miRNAs obtained by an analysis with a microchip/microarray as well as the sensitivity and accuracy of the results. It is especially significant that, in the Examples of the present application, the difference between the levels of patients and of healthy individuals (reference value) detected with this qPCR technique is less than with the microchip technique, so when the levels of miRNAs are determined utilizing qPCR and the reference value for each miRNA is the average of the level thereof in healthy individuals, it will be preferred to determine that a decrease of at least two times the level of the analyzed sample compared to the reference value be sufficient to establish that the level of an miRNA is less than its corresponding reference value.

Alternatively, an additional embodiment can be used, which consists of the indirect detection of the miRNAs based on the alteration of the expression of its target genes, whether by quantification of the messenger RNAs of said genes or the quantification of the proteins that codify: the decrease of the levels of an miRNA should involve a lesser degradation of the messenger RNAs that are its target, which should result in increased levels of the corresponding proteins. The mediator transcription factors of the transcription, and thus of the expression of the miRNAs, could also be used.

Currently different programs have been developed to predict target genes of miRNAs, such as the TargerMiner tool, available at www.isical.ac.in/~bioinfo_miu (Bandyopadhyay S, Mitra R, "TargetMiner: microRNA target prediction with systematic identification of tissue-specific negative examples", Bioinformatics. 2009 Oct. 15; 25(20):2625-31, doi: 10.1093/bioinformatics/btp503. Epub 2009 Aug. 19.PubMed PMID: 19692556); the PICTAR-VERT tool, available at http://pictar.mdc-berlin.de/ (Krek A, Grün D, Poy M N, Wolf R, Rosenberg L, Epstein E J, MacMenamin P, da Piedade I, Gunsalus K C, Stoffel M, Rajewsky N, "Combinatorial microRNA target predictions. Nat Genet. 2005 May; 37(5):495-500. Epub 2005 Apr. 3. PubMed PMID: 15806104), or the COMIR tool, available at http://www.benoslab.pitt.edu/comir/ (Coronello C, Benos P V., "ComiR: Combinatorial microRNA target prediction tool", Nucleic Acids Res. 2013 July; 41(Web Server issue):W159-64. doi: 10.1093/nar/gkt379, Epub 2013 May 22, PubMed PMID: 23703208; PubMed Central PMCID: 15806104). In any case, if this alternative is used, it is recommended that the potential target transcripts be experimentally validated in the type of cell of interest, due, among other reasons, to the lack of absolute complementarity between the sequences of the miRNAs of animals and those of their corresponding targets and to other specific factors of tissue or cellular type.

As has already been mentioned, for the purposes of the present invention the variation of the levels of miRNA is taken into account when said levels are reduced by at least two times compared to the reference value or control value of healthy individuals. In cases where a more restrictive criterion is needed, the variation in the levels of the miRNA will be taken into account when said levels are reduced by at least four times compared to the reference value or control value of healthy individuals. In cases where an even more restrictive criterion is needed, the variation in the levels of the miRNA will be taken into account when said levels are reduced by at least six times compared to the reference value or control value of healthy individuals. When the minimum variation value that should be observed is established, it is important to take into account not only how accurate the diagnosis is to be, but also the technique used to determine the levels of the miRNAs, so that the established value is compatible with the differences that said technique makes it possible to observe.

The individual on whom the diagnosis is carried out is preferably a human being. In that case, the miRNAs among which the label or labels will be selected for their measurement, the decrease of which by a certain degree (according to the different embodiments) compared to its corresponding reference value will be indicative of fibromyalgia, as well as the possible optional controls utilized to confirm the diagnosis, will be the corresponding human miRNAs, specifically those which currently have the names hsa-miR-223-3p (miR-223), hsa-miR-451a (miR-451), hsa-miR-338-3p (miR-338), hsa-miR-143-3p (miR-143), hsa-miR-145-5p (miR-145), hsa-miR-21-5p (miR-21), hsa-miR-1908-5p (miR-1908), hsa-miR-1260b (miR-1260b), which are the miRNAs analyzed in the Examples of the present invention.

The names of some miRNAs have been changing over time. Thus, for example, the names that are in the database corresponding to the microarray utilized in Example 1 in some cases do not correspond with the current names, there being small variations in the indicación about the arm of the hairpin from which they originate. Considered as the "current" name of the human miRNAs analyzed in the Examples of the present application is the one identifying the miRNAs in the current version of the database "miRBase" (http://www.mirbase.org/, Version 21 of June 2014). However, the respective entries of each miRNA in said database also contain the former name of said miRNA, which is the one that can be found in many publications. Thus, for reasons of clarity, indicated in the following Table is the current nomenclature of each of the miRNAs analyzed in the Examples of the present application, its former name, the name they had according to the database of the supplier of the microarray at the time the assays were performed, the sequence of each of the human miRNAs, its access number in the "miRBase" database, as well as the sequence number with which they appear in the list of sequences of the present application:

TABLE 1

Analyzed human microRNAs: sequence and access number to said sequence

| Name of the MicroRNA | Former name | Name in microarray | Access No. miRBase | Sequence of the Mature miRNA | SEQ ID NO: |
|---|---|---|---|---|---|
| hsa-miR-223-3p | hsa-miR-223 | hsa-miR-223 | MIMAT0000280 | UGUCAGUUUGUCAAAUACCCCA | 1 |
| hsa-miR-451a | hsa-miR-451 | hsa-miR-451 | MIMAT0001631 | AAACCGUUACCAUUACUGAGUU | 2 |
| hsa-miR-338-3p | hsa-miR-338 | hsa-miR-338-3p | MIMAT0000763 | UCCAGCAUCAGUGAUUUUGUUG | 3 |
| hsa-miR-143-3p | hsa-miR-143 | hsa-miR-143 | MIMAT0000435 | UGAGAUGAAGCACUGUAGCUC | 4 |
| hsa-miR-145-5p | hsa-miR-145 | hsa-miR-145 | MIMAT0000437 | GUCCAGUUUUCCCAGGAAUCCCU | 5 |
| hsa-miR-21-5p | hsa-miR-21 | hsa-miR-21p | MIMAT0000076 | UAGCUUAUCAGACUGAUGUUGA | 6 |
| hsa-miR-1908-5p | hsa-miR-1908 | hsa-miR-1908 | MIMAT0007881 | CGGCGGGGACGGCGAUUGGUC | 7 |
| hsa-miR-1260b | hsa-miR-1260b | hsa-miR-1260b | MIMAT0015041 | AUCCCACCACUGCCACCAU | 8 |

Thus, the tests for their determination will be designed taking into account the sequences of the miRNAs, which can also be consulted in the different databases where they are available, such as: the "micro-RNA Target Collection" On the Memorial Sloan-Kettering Cancer Center (http://cbio.mskcc.org/mirnaviewer/, which also allows consulting about targets of human miRNAs: http://cbio.mskcc.org/miRNA2003/mammalian/index.html), "miRecords" (www.biolead.org) and especially the database of the Wellcome Trust Sanger Institute "miRBase" (http://www.mirbase.org/) already previously cited, in which are based the assays performed in the Examples of the present application.

In a preferred embodiment of the invention, when the individual on whom the diagnosis is carried out is a human being, and the determination of the level of the selected microRNAs is done by quantitative PCR with prior retrotranscription (reverse transcription), the forward primers of the quantitative PCR will be selected from the group of: SEQ ID NO:9 (for hsa-miR-223-3p), SEQ ID NO:10 (for hsa-miR-451a), SEQ ID NO:11 (for hsa-miR-338-3p), SEQ ID NO:12 (for hsa-miR-143-3p), SEQ ID NO:13 (for hsa-miR-145-5p), SEQ ID NO:14 (for hsa-miR-21-5p), SEQ ID NO:15 (hsa-miR-1908-5p), SEQ ID NO:16 (for hsa-miR-1260b)

In any of the previous embodiments, or more preferably, in connection with any of the embodiments in which the level is measured of at least four of the miRNAs selected from the group of miR-223, miR-451, miR-338, miR-143 and miR-145, or from the cited group of five miRNAs, and it has been decided that the patient suffers from the disease of fibromyalgia if the level of at least two of the measured miRNAs have a value lower than their respective reference value, the method can comprise an additional step in which it is determined if a patient diagnosed with fibromyalgia presents with a low level of mental fatigue. That conclusion will be reached when, from the group miR-223, miR-451, miR-338, miR-143 and miR-145, only the levels of the microRNAs miR-451 and miR-338 have a level more than their corresponding reference values. Preferably, as in other embodiments, the levels will also be analyzed of the negative controls miR-21, miR-1260b and miR-1908 and it will be determined that the patient diagnosed with fibromyalgia presents with a low level of mental fatigue if, in addition to the criterion referring to the microRNAs miR-451 and miR-338, at least two of the negative controls have levels with lower values than their corresponding reference values.

Given the importance fibromyalgia is gaining in hindering work activity, this additional step to the diagnostic method could be useful for differentiating patients who can carry out certain intellectual activities and those who have serious difficulties with them, determining whether or not it is necessary for a patient to be given leave from work depending on the functions they perform at work.

The invention will now be explained in more detail by means of the Examples and Figures that are set forth below.

EXAMPLES

The tests that are described in the present Examples were carried out with the individuals and their samples as described below, together with the statistical tools used for their analysis.

A. Participants in the Study

Between January and April 2011, 75 patients and 79 healthy controls were recruited consecutively and transversely, paired by age range (+1-5 years), all of them from a single institution: the Faculty of Medicine of the Catholic University of Valencia.

Due to the nature of the disease of fibromyalgia (FM), special consideration was given to the selection of patients who participated in the development of the diagnostic method in order to limit possible bias during the interpretation of the results. The 75 patients participating in the study were recruited through an event to promote the study at AVAFI (Valencia Association of Fibromyalgia Sufferers), where the objectives of the study and the analyses required for their performance were reported in detail. All of the patients met the criteria of the American College of Rheumatology (1990). FM patients previously diagnosed by their specialist practitioners (SP) who were interested in participating did so by going to the University Clinics of the "San Vicente Mártir" Catholic University of Valencia on the announced dates.

The patients were provided with a sheet with information about the study, and all those who, after being informed, agreed to participate therein were asked to sign the respective informed consent, which they had the right to revoke at any time should they so desire.

The confidentiality of the participants was maintained at all times in accordance with Organic Law 15/1999 of December 13, Protection of Personal Information. Each of the participants was assigned a numerical code that was maintained on all of the fractions that derived from their sample.

The inclusion and exclusion criteria for the patients were as follows:

A.1. Inclusion Criteria:

Subject 18 years old or more, with prior diagnosis of fibromyalgia (FM) according to the criteria described by the American College of Rheumatology (Wolfe et al., "The American College of Rheumatology 1990 Criteria for the Classification of Fibromyalgia. Report of the Multicenter Criteria Committee", Arthritis Rheum. 1990, 33(2):160-172), with a history of generalized pain and pain at specific anatomical points on digital palpation.

The pain is considered generalized when there is pain on the right and left sides of the body and pain above and below the waist. Moreover, there should be axial skeletal pain (cervical spine, or anterior region of the thorax, or dorsal spine, or lower part of the shoulder). In this definition, shoulder and buttock pain is considered within pain of the right or left side of the body. Pain in the lower part of the shoulder is considered as pain of the lower segment.

There should be pain upon digital palpation in at least 11 of the 18 following sensitive points:
  Occipital: Bilateral. At the suboccipital muscle insertions.
  Lower cervical: Bilateral. In the anterior portions of the transverse interapophysiary spaces of C5-C7.
  Trapezium: Bilateral. In half of the upper edge.
  Supraspinatus: Bilateral. At its origin, above the scapular spine near the medial border.
  2nd rib: Bilateral. At the 2nd costochondral joint just lateral in relation to the joints of the surfaces located above.
  Lateral epicondyle: Bilateral, 2 cm distal to the epicondyles.
  Gluteus: Bilateral. In the upper outside quadrant of buttock, in the anterior fold of the muscle.
  Greater trochanter: Bilateral, posterior to the trochanteric prominence
  Knee: Bilateral. In the medial adipose pad proximal to the articular margin.

The digital palpation should be done with the force of approximately 4 kg. In order for the sensitive point to be considered positive, the patient must indicate that the palpation is painful. Sensitive should not be considered painful.

A patient with the disease of fibromyalgia must meet both criteria of generalized pain and point pain upon palpation. Generalized pain must have been present for at least three months. The presence of a second clinical disease does not exclude a diagnosis of fibromyalgia.

It was required that the diagnosis of the FM patients participating in the study had included a complete analysis to discard an alternative origin of their pains: complete blood count with differential count of leukocytes, reactive protein C, rheumatoid factor, alanine aminotransferase, albumin, alkaline phosphatase, aspartate aminotransferase, total bilirubin, calcium, carbon dioxide, chlorine, creatinine, glucose, potassium, total proteins, sodium, urea nitrogen, TSH, free T3, free T4, thyroglobulin, CMV ac. IgG, HBcAc, HBsAc, Hepatitis C.

All study variables were stored on an Access 2003 database (Microsoft®, Redmond, Wash., USA).

A.2. Exclusion Criteria:

Subject less than 18 years old with the existence of associated pain syndrome, existence of other rheumatological diseases or other serious disease not associated with FM.

The healthy participants were donor subjects, 18 years old or more, from the Valencia Community Transfusion Center, paired by age with a margin of 5 years with the patients, selected by the usual Transfusion Centers screening procedures in their blood donation campaigns, using the "buffy-coats" from the donation bags as biological sample. The number of healthy participants was 79.

B. Confirmation of Diagnosis and Additional Tests to which the Participating Patients were Subject The diagnosis of fibromyalgia of the participants in the study was confirmed by means of interview, taking of data that were included in a clinical history Access database and medical physical examination consisting of digital palpation and confirmation of pain in at least 11 of the 18 sensitive points, according to the requirements of the American College of Rheumatology (Wolfe et al., 1990, see previous quote) already detailed in previous paragraphs.

Thus, all of the patients underwent a clinical visit to evaluate the clinical criteria and severity of their fibromyalgia. In addition, the diagnostic confirmation of fibromyalgia after the clinical evaluation of their physician from the health centres of origin included the scores obtained from the evaluation of the participants by means of validated psychometric questionnaires ("case report forms").

Specifically, the psychometric questionnaires that were used were:
a) Fibromyalgia Impact Questionnaire (FIQ) (Rivera J, González T, "The Fibromyalgia Impact Questionnaire: a validated Spanish version to assess the health status in women with fibromyalgia", Clin Exp Rheumatol., 2004 September-October, 2285):554-60; Burckhardt C S et al., "The fibromyalgia impact questionnaire: development and validation", J Rheumatol. 1991, 18(5):728-33).
b) Multidimensional Fatigue Questionnaire (MFI) for the evaluation of fatigue according to the Fatigue Intensity Scale (FIS) designed by Krupp and Associates (Krupp et al., "The fatigue severity scale. Application to patients with multiple sclerosis and systemic lupus erythematosus", Arch Neurol. 1989; 46(10):1121-3).
c) Health and well-being questionnaire (SF36) (Ware J E, Jr., Sherbourne C D, "The MOS 36-item short-form health survey (SF-36). I. Conceptual framework and item selection", Med Care 1992; 30:473-483; Bullinger M et al, "[SF-36 Health Survey in Rehabilitation Research. Findings from the North German Network for Rehabilitation Research, NVRF, within the rehabilitation research funding program]", Rehabilitation (Stuttg). 2003, 42(4):218-25).

Patients with a score equal to or greater than the median of the general population with respect to asthenia or a reduction of activity according to the MFIs scales fulfilled criteria according to the definition of 1994 consensus cases (http://www.cdc.gov/cfs/case-defnition/1994.html, revised 9, Jun. 14).

The control group was composed of healthy blood donor patients from the Valencia Community Transfusion Center.

The complete blood sample was obtained per individual after the informed consent was signed.

The demographic, clinical and biological variables were entered into an Access 2003 (Microsoft®, Redmond, Wash., USA) database with anonimization of the samples according to the criteria established by the LOPD (Organic Law 15/1999).

This study was approved by the Clinical Trials and Research Committee (CEIC) of the Plana Hospital in Vila-Real, Castellón, Spain.

As a criterion for selection of the 11 patients subject to molecular analysis, they had to present with at least 16 points of pain.

C. Taking of Samples, Processing and Storage

C.1. Sample Taking

The taking only of blood from participating FM patients consisted in a final volume of approximately 20 cc/patient, and was done by venipuncture in 2 Vacutainer Tubes each containing 170 IU of lithium heparin as anticoagulant (Becton Dickinson BD 365725).

All samples were processed within less than two hours after extraction, maintaining the samples at ambient temperature (AT) during that period.

In the case of control samples, the volume of buffy coats (fraction of a blood sample to which an anticoagulant has been added, obtained after density gradient centrifugation of the blood, and which contains most of the white blood cells and platelets) was greater than 20 cc/donor. The samples were also processed within two hours after collection at the Valencia Community Transfusion Center, maintaining the samples at AT (ambient temperature) up to the time of processing.

C.2. Preparation of miRNAs from Peripheral Blood

C.2.1 Isolation of PBMCs (Peripheral Blood Mononuclear Cells).

BD VacutainerCPT Mononuclear Cell Preparation 362753 Tubes with Sodium 120 USP Heparine were used for the isolation of the PBMCs, following the manufacturers instructions (Becton Dickinson).

The tubes were inverted 8-10 times to mix the blood prior to centrifugation. The centrifugation was done in an Eppendorf model 5810R centrifuge with swing-bucket rotor programmed at 1800 g for 15-20 min at AT, with no acceleration and braking.

After separation of fractions, the plasma was aliquoted in cryo-tubes which, after labeling, were preserved at −80° C. The ring or layer of mononuclears ("buffy coat") was carefully aspirated with a pipette with a wide bore and was placed in a clean 15 ml tube in order to proceed with the lysis of possible erythrocyte contaminants. They were incubated on ice with 1 volume of erythrocyte lysis buffer (155 mM $NH_4Cl$, 10 mM $NaHCO_3$, pH 7.4, 0.1 mM EDTA) for 5 minutes, and were centrifuged again at 500 g for 10 minutes at AT, this time with rotor braking, to eliminate the breakage waste from the supernatant.

Finally, the PBMCs were subjected to two washes in PBS buffer solution (pH 7.4 saline solution; 1 volume) by resuspension followed by centrifugation at 300 g for 15 minutes at AT.

The pellets were resuspended in a freezing medium consisting of a mixture of 90% fetal bovine serum (FBS) and 10% dimethyl sulfoxide (DMSO) as cryo-protector agent. To count viable cells, a 10 μl sample was taken with 50% Trypan Blue and the counting was done with a Neubauer Camera. The concentration of PBMCs was adjusted to $10^7$ cells/ml, and after it was aliquoted into 0.5 ml cryovials, they were stored at −150° C. until they were used.

These procedures were carried out under sterile conditions utilizing a AV-100 Telstar Ref. 23812 culture hood with ultraviolet lamp.

C.2.2 Obtaining miRNAs

The extraction of total RNA including the miRNAs and other small size RNAs was done using the mirVana™ (Ambion, cat #AM1560) isolation kit following the manufacturers recommendations.

The concentrations and integrity of the isolated total RNA were obtained by spectrophotometric analysis (Nanodrop 200, ThermoScientific) (see Table 2 below, which shows the values of the concentrations calculated by the system) and by electropherogram (Eukaryote Total RNA Nano chips and the systems 2100 Bioanalyzer, Agilent Technologies; and Agilent 2100 Expert Software, Agilent Technologies) according to the product's instructions. Samples were selected whose profiles showed integrity of the extracted RNA, either because samples were involved whose RIN (RNA Integrity Number: integrity value of the RNA, calculated with the aforementioned Agilent software as discussed on the Web page: http://www.genomics.agilent.com/article.jsp?pageId=2181&_requestid=266525), exceeded the value of 7.0 or, in those cases in which the system did not offer a calculation of the RIN number (something that occurs sometimes with samples that are not degraded), the spectrum of the sample was assessed, choosing those in which the spectrum was compatible with non-degraded samples. Said analysis was performed at the Genomic Unit of the Experimental Research Central Support Department (SCSIE) of the University of Valencia, and was confirmed by Toray Industries (Japan) on samples that were sent to them.

Once the results of the analysis by microarrays was received, they were analyzed again by electropherogram, by the aforementioned Agilent systems (2100 Bioanalyzer, Agilent Technologies; and Agilent 2100 Expert Software, Agilent Technologies), the aliquotes of the total RNA samples preserved in Valencia to ensure their quality before proceeding with the analysis by qPCR.

The relative abundance of miRNAs (% miRNA) in the total RNA preparations was determined by the "small RNA kits" of the 2100 Bioanalyzer (Agilent Technologies) and the corresponding Agilent 2100 Expert Software (Agilent Technologies), per the instructions for the product, at the Genomic Unit of the Experimental Research Central Support Department (SCSIE) of the University of Valencia. The values obtained are also included in Table 2 below.

TABLE 2

Concentration, integrity and purety of the analyzed total RNA preparations.

| Sample | Concentration (ng/μl) | $A_{260}/A_{280}$ | $A_{260}/A_{230}$ | RIN | miRNA (%) |
|---|---|---|---|---|---|
| Controls: | | | | | |
| C1 | 168 | 1.98 | 2.31 | N/A* | 10 |
| C2 | 182.5 | 2.03 | 1.62 | 8.1 | 12 |
| C3 | 187.4 | 2.06 | 2.17 | 8.4 | 15 |
| C4 | 341.9 | 2.06 | 2.05 | 8.3 | 15 |
| C5 | 195.4 | 2.02 | 2.15 | 7.4 | 15 |
| C6 | 184.8 | 2 | 2.2 | 8.3 | 13 |
| C7 | 187.1 | 2.07 | 2.14 | 8.5 | 15 |
| C8 | 200.1 | 1.94 | 2.15 | N/A | 21 |
| C9 | 189 | 2.02 | 2.24 | 7.2 | 16 |
| C10 | 191.6 | 2.02 | 2.2 | 7.7 | 8 |
| Patients: | | | | | |
| FM1 | 176.6 | 1.94 | 2.15 | N/A* | 14 |
| FM2 | 183.6 | 1.94 | 2.14 | 10 | 16 |
| FM3 | 185.3 | 1.94 | 1.86 | 10 | 11 |
| FM4 | 166.9 | 1.93 | 2.15 | 10 | 39 |
| FM5 | 188 | 1.96 | 1.49 | N/A* | 18 |
| FM6 | 165.5 | 1.94 | 2.19 | 10 | 4 |
| FM7 | 118.8 | 1.92 | 2.27 | N/A* | 16 |
| FM8 | 164.7 | 1.96 | 2.15 | 10 | 19 |
| FM9 | 179.2 | 1.93 | 2.1 | N/A* | 30 |
| FM10 | 177 | 1.91 | 2.22 | N/A* | 6 |
| FM11 | 174 | 1.93 | 2.13 | N/A* | 4 |

*N/A: Not analyzed by the apparatus: analyzed from the spectrum by technical personnel D. Statistical Analysis The results were expressed in percentages comparing the diseased population to the control population. To determine the correlation between qualitative variables, the Chi-square test was used. To determine the correlation between quantitative variables, the Mann-Whitney U test was used. The differences between groups were considered significant if $p<0.05$. The statistical analysis was performed with the SPSS 13.0 package (SPSS Inc, Chicago, Ill., USA).

Example 1: Analysis of the Expression of miRNAs by Microarray Technology 1.1. Results Obtained from the Microarrays and Analysis Thereof The total RNAs extracted from PBMCs of 11 FM patients and 10 control subjects were sent to Japan (Toray Industries) in dry ice by a courier transport, where they were analyzed. The fractions were reanalyzed by electropherogram, confirming that all of the samples analyzed had profiles compatible with integrity of the extracted RNA, most of them having an RIN of more than 7.0.

The labeling of the total RNA was done by Hy5™ fluorescent labeling with the miRCURY LNA Array miR kit (Exiqon, Vedbaek, Denmark). The labeled RNAs were hybridized in microarrays, 3D-Gene Human miRNA Oligo chips (v.16.0; Toray Industries, Tokyo, Japan). The annotation and sequences of the probes of oligonucleotides of these array systems are in conformity based on miRBase Release 16 (http://microrna.sanger.ac.uk/sequences/). After rigorous washing, the fluorescent signals were scanned with a 3D-Gene Scanner (Toray Industries) and analyzed with the help of 3D-Gene Extraction software (Toray Industries).

Each chip showed a similar pattern with respect to signal distribution (FIG. 1), so overall normalization of the data can be adapted. The data recorded at each point were standardized using the mean intensity of background noise determined from all of the targets of the array with confidence intervals of 95%. Measurements of the duplicates, the signals of which exceeded values of more than 2 standard deviations (2SD) in reference to the background noise, were considered valid. The levels of expression relative to a specific miRNA were calculated by comparison of means of the valid duplicates obtained with reference to their experimental average value of the microarray. The data were generally standardized by array, adjusting the median of the intensity signal to 25.

The analysis of the data obtained on the levels of miRNAs of the 11 FM patients and 10 healthy donors paired by age (+/−5 years) by means of 3D-Gene Human miRNA Oligo chips (v.16.0; Toray Industries, Tokyo, Japan) microarray technology, showed a marked predominance of lower levels of miRNAs than those found in the control subjects. Specifically, 16% of the analyzed miRNAs (193/1212) showed at least a 50% reduction and 3% of the miRNAs (40/1212) a reduction of 75% or more.

For the preparation of the heatmap of the microarrays the miRNAs were selected that had differences between the control group (C) and patients (FM) greater than 4 times. A heatmap is a graphic representation of the data in which the individual values contained in a matrix are represented as colors. In this case, the program used for producing the heat map was R 3.0.2 [R Core Team (2013). R: A language and environment for statistical computing. R Foundation for Statistical Computing, Vienna, Austria. URL http://www.R-project.org/].

Figure 2:
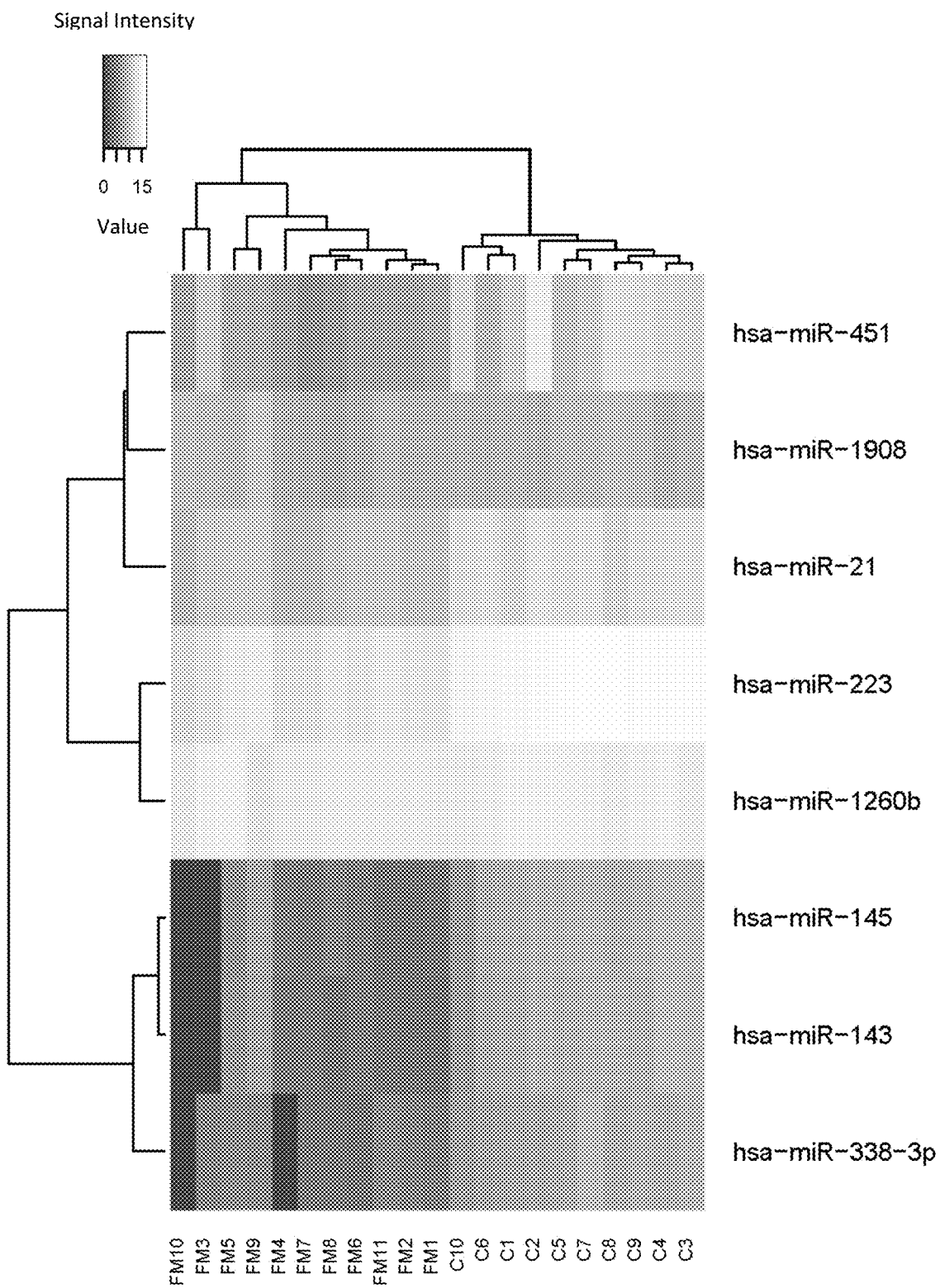
FIG. 2. "Heatmap" or set of microRNAs analyzed by microarray showing the microRNAs with marked intensity differences between patients and controls with which it was decided to continue the study. The grayscale corresponds to decreasing intensity values, on a scale of 0-15, based on the average of intensities of the microarray, expressed as power of 2, and taking the exponent of said power (the base 2 logarithm) as value of the scale. The areas represented with darker shading (4) correspond to lower intensity values (0) while the lighter areas correspond to readings with higher values (15) over the average intensity obtained after the global standardization of values from the microarray.

The heatmap obtained is represented in FIG. 2, In which the original tones (which vary from red to orange and yellow in the original) appear represented in grayscale so that the darker tones correspond to values of lower intensity of the detected signal after overall normalization of values of the microarray.

From among the inhibited miRNAs, those were selected that had a more marked inhibition, specifically those that had inhibition 6-13 times less than the levels of healthy subjects, for their validation by real-time PCR. Said microRNAs were the human microRNAs miR-451, miR-338-3p, miR-143, miR-145 and miR-223 (hsa-miR-451a, hsa-miR-338-3p, hsa-miR-143-3p, hsa-miR-145-5p, hsa-miR-223-3p, which are named in the database of Toray Industries corresponding to the microarray as hsa-miR-451, hsa-miR-338-3p, hsa-miR-143, hsa-miR-145, hsa-miR-223. Four of them were selected because they had averages that were more different between fibromyalgia patients and controls; in the case of the miR-223 the distance was less, but the signal reading was higher. In Table 3 below, the data are shown of the individual intensity readings for each of the participants, obtained from the 3D-Gene Human miRNA Oligo chips (v.16.0; Toray Industries, Tokyo, Japan) microarrays, after their overall normalization, for the 5 miRNAs inhibited at levels 6 or more according to the arithmetic mean, using the nomenclature of the microarray.

TABLE 3

Data from the microarrays of the 5 biomarker miRNAs after overall normalization

| Sample | hsa-miR-451 | hsa-miR-338-3p | hsa-miR-143 | hsa-miR-145 | hsa-miR-223 |
|---|---|---|---|---|---|
| C1 | 2227.486665 | 264.158394 | 375.810287 | 473.615044 | 51653.58662 |
| C2 | 19593.32011 | 267.717549 | 582.351337 | 567.217323 | 61996.61509 |
| C3 | 3301.83803 | 550.424219 | 781.253618 | 852.589258 | 77138.77704 |
| C4 | 3730.193074 | 428.644897 | 815.749709 | 824.653082 | 72748.40494 |
| C5 | 1146.573847 | 343.727175 | 492.042899 | 589.576509 | 77202.87996 |
| C6 | 683.433897[a] | 199.506422 | 319.849416 | 380.558555 | 39896.82884 |
| C7 | 1889.092475 | 743.848307 | 604.228968 | 638.500033 | 88579.28544 |
| C8 | 7335.509779 | 357.198588 | 502.167721 | 484.688854 | 86658.50076 |
| C9 | 5135.832295 | 459.920309 | 474.336505 | 533.642298 | 76955.8396 |
| C10 | 3257.458249 | 126.838433[a] | 114.763235[a] | 115.432316[a] | 34539.07342[a] |
| FM1 | 305.834489 | 26.318745 | 15.177271 | 18.555039 | 10111.73509 |
| FM2 | 206.559244 | 32.832642 | 16.001444 | 16.108543 | 11116.44533 |
| FM3 | 1734.445699 | 32.143672 | [b] | [b] | 7050.559134 |
| FM4 | 161.655279 | [b] | 20.372658 | 28.646992 | 6314.357339 |
| FM5 | 330.340215 | 53.035094 | 82.148401 | 75.426581 | 16817.24877 |
| FM6 | 202.124686 | 16.338276 | 24.650354 | 25.399775 | 9053.612596 |
| FM7 | 78.315045 | 17.962685 | 22.405244 | 20.470409 | 5860.535658 |
| FM8 | 119.190489 | 19.81887 | 16.264705 | 38.761781 | 11742.76138 |
| FM9 | 337.022127 | 47.754941 | 194.84006 | 233.920951 | 19213.67863 |
| FM10 | 259.317146 | [b] | [b] | [b] | 4221.946537 |
| FM11 | 210.059273 | 43.730618 | 16.916919 | 15.923472 | 14852.24993 |

[a]The underlined values correspond to the lower limit of the range of control values.
[b]The boxes in white correspond to missing reading determinations miRNAs were selected as control that had differences in levels of expression less than 4 times: hsa-miR-1260b, hsa-miR-1908-5p and hsa-miR-21-5p, which are called in the microarray hsa-miR-1260, hsa-miR-1908 and hsa-miR21. In Table 4 below, the data are shown of the individual intensity readings for each of the participants, obtained from the 3D-Gene Human miRNA Oligo chips (v.16.0; Toray Industries, Tokyo, Japan) microarrays, after their overall normalization, for the 3 miRNAs inhibited at levels 4 times according to the arithmetic mean, using the nomenclature of the microarray.

TABLE 4

Data from the microarrays of the 3 miRNAs selected as possible negative markers, after overall normalization

| Sample | hsa-miR-21 | hsa-miR-1260b | hsa-miR-1908 |
|---|---|---|---|
| C1 | 3360.142615 | 28151.8309 | 672.614777 |
| C2 | 7785.488521 | 29881.7485 | 573.149245 |
| C3 | 6610.461283 | 18698.6661 | 781.557803 |
| C4 | 5658.2508 | 28255.2295 | 581.519534 |
| C5 | 5343.510235 | 26120.276 | 896.785265 |
| C6 | 6043.767411 | 20401.0122 | 568.902254[a] |
| C7 | 6999.363226 | 25526.4404 | 852.633589 |
| C8 | 3001.680858[a] | 19382.0309 | 1122.87105 |
| C9 | 5187.202282 | 23852.3069 | 953.236029 |
| C10 | 4710.493502 | 16492.401[a] | 622.69169 |
| FM1 | 1241.750335 | 16416.3459 | 554.24173 |
| FM2 | 1304.220922 | 19216.0524 | 514.93731 |
| FM3 | 1626.655657 | 24312.6231 | 840.11438 |
| FM4 | 757.147795 | 15735.7582 | 445.864872 |

TABLE 4-continued

Data from the microarrays of the 3 miRNAs selected as possible negative markers, after overall normalization

| Sample | hsa-miR-21 | hsa-miR-1260b | hsa-miR-1908 |
|---|---|---|---|
| FM5 | 2096.750386 | 26072.6375 | 659.583933 |
| FM6 | 1840.144328 | 19454.8228 | 406.420377 |
| FM7 | 783.224453 | 15751.1767 | 401.503764 |
| FM8 | 1360.727881 | 17345.3276 | 292.404162 |
| FM9 | 2102.365502 | 7877.05237 | 1420.53831 |
| FM10 | 753.048593 | 11333.0003 | 982.798912 |
| FM11 | 1638.51156 | 17409.8649 | 746.514169 |

$^a$The underlined values correspond to the lower limit of the range of control values.

Table 5 below summarizes the average levels of said eight miRNAs (the five with inhibition levels of more than 4 and the three that had inhibition levels less than said value) in the healthy controls and in the fibromyalgia patients, as well as the relation between both average values. Again, the nomenclature of the microarray was used for the miRNAs.

TABLE 5

Average values of the levels of the selected miRNAs in the assays of microarrays for the method of diagnosing fibromyalgia (FM) patients

| miRNA | Average Controls | Average FM | Average C/Average FM |
|---|---|---|---|
| hsa-miR-143 | 506.26 | 45.42 | 11.15 |
| hsa-miR-145 | 546.05 | 52.58 | 10.39 |
| hsa-miR-223 | 66736.98 | 10577.74 | 6.31 |
| hsa-miR-338-3p | 374.2 | 32.22 | 11.62 |
| hsa-miR-451a | 4830.07 | 358.62 | 13.47 |
| hsa-miR-1260b | 23676.19 | 17356.79 | 1.36 |
| hsa-miR-1908 | 762.6 | 660.45 | 1.15 |
| hsa-miR-21 | 5470.04 | 1409.5 | 3.88 |

With the data from Tables 3 and 4 above, the inhibition levels, at the individual level, were obtained on the 5 selected fibromyalgia marker miRNAs and of the 3 possible negative controls. Said inhibition levels were calculated as the ratio of values from the values obtained in 3D-Gene Human miRNA Oligo chips microarrays (v.16.0; Toray Industries, Tokyo, Japan) after overall normalization of each patient with reference to the lower reading value of the range of values of the controls. Said lower values are those that are underlined in Tables 3 and 4 above.

The values obtained for the inhibition levels calculated in this way are shown below in Table 6 (fibromyalgia marker miRNAs) and Table 7 (possible negative control miRNAs).

TABLE 6

Individual inhibition levels of the 5 miRNAs selected as possible fibromyalgia markers.

| Patient | hsa-miR-451 | hsa-miR-338-3p | hsa-miR-143 | hsa-miR-145 | hsa-miR-223 |
|---|---|---|---|---|---|
| FM1 | 2.23 | 4.82 | 7.56 | 6.22 | 3.42 |
| FM2 | 3.31 | 3.86 | 7.17 | 7.17 | 3.11 |
| FM3* | 0.39# | 3.95 | | | 4.90 |
| FM4 | 4.23 | | 5.63 | 4.03 | 5.47 |
| FM5 | 2.07 | 2.39 | 1.40# | 1.53# | 2.05 |
| FM6 | 3.38 | 7.76 | 4.66 | 4.54 | 3.81 |
| FM7 | 8.73 | 7.06 | 5.12 | 5.64 | 5.89 |
| FM8 | 5.73 | 6.40 | 7.06 | 2.98 | 2.94 |
| FM9 | 2.03 | 2.66 | 0.59# | 0.49# | 1.80# |
| FM10* | 2.64 | | | | 8.18 |
| FM11 | 3.25 | 2.90 | 6.78 | 7.25 | 2.33 |

*Patients with only two of the five miRNAs inhibited at 2 times
Underlined values: no inhibition or inhibition that does not exceed the value of 2 times

TABLE 7

Individual inhibition levels of the 3 miRNAs selected as possible negative markers.

| Patient | hsa-miR-21 | hsa-miR-1260b | hsa-miR-1908 |
|---|---|---|---|
| FM1* | 2.42# | 1.00 | 1.03 |
| FM2* | 2.30# | 0.86 | 1.11 |
| FM3 | 1.85 | 0.68 | 0.68 |
| FM4* | 3.96# | 1.05 | 1.29 |
| FM5 | 1.43 | 0.63 | 0.87 |
| FM6 | 1.63 | 0.85 | 1.41 |
| FM7* | 3.83# | 1.05 | 1.43 |
| FM8* | 2.21# | 0.95 | 1.96 |
| FM9* | 1.43 | 2.09# | 0.40 |
| FM10* | 3.99# | 1.46 | 0.58 |
| FM11 | 1.83 | 0.95 | 0.77 |

*Patients with only two of the three miRNAs not inhibited or with inhibition that does not reach the value of 2 times
Underlined values: inhibition that exceeds the value of 2 times

1.2. Relative Abundance of miRNAs

In order to avoid possible bias derived from differences in miRNA extraction yield compared to larger RNA, which could lead to an erroneous conclusion of inhibition or generalized overexpression, the relative abundance of miRNAs was evaluated in each of the total RNA preparations analyzed.

As summarized in Table 2 ("miRNAs %" column) the average relative abundance in control preparations of PBMCs (14%) is similar to that of total RNA preparations of PBMCs from FM patients (16%). Although the range of relative abundances of miRNAs in preparations from patients (4-39%) is greater than that of relative abundances of miRNAs in controls (8-21%), this could not justify the differences detected in average relative abundances of up to 13 times for some miRNAs (see Table 5, hsa-miR-451).

After this verification, the five miRNAs that had the most marked inhibition (between 6-13 times less than the levels of healthy subjects) were selected for validation by real-time PCR. The above-mentioned miRNAs with differences in levels of expression of less than 4 times, hsa-miR-21, hsa-miR-1908, hsa-miR-1260b, were selected as control.

Example 2: Analysis of the Expression of miRNAs by Microarray Technology

2.1. Amplification of miRNA Sequences by Means of qRT-PCR (Quantitative-Reverse Transcribed-PCR) Amplification The retrotranscription of the total RNA extracted was done using the miScript II RT (Qiagen, cat #218161) kit, following the manufacturers instructions. The cDNAs (complementary DNAs) obtained from said reverse transcription process were amplified by real-time PCR or quantitative PCR using the miScript SYBR Green PCR (Qiagen, cat #218073) kit. The sequences of the forward primers used for the assay are shown in Table 8, together with the sequence number corresponding to it in the attached list; the reverse primer was common to all of the amplifications corresponding to the universal primer (UP) provided by the manufacturer of the kit, and of unknown sequence.

TABLE 8

List of forward primers used to amplify the selected miRNAs

| Name of the target miRNA | Sequence of the Mature miRNA | Sequence of the forward primer (5'-3') | Tm* (° C.) | SEQ ID NO: |
|---|---|---|---|---|
| hsa-miR-223-3p | UGUCAGUUUGUCAAAUACCCCA | TGTCAGTTTGTCAAATACCC | 50.3 | 9 |
| hsa-miR-451a | AAACCGUUACCAUUACUGAGUU | AAACCGTTACCATTACTGAG | 49.8 | 10 |
| hsa-miR-338-3p | UCCAGCAUCAGUGAUUUUGUUG | TCCAGCATCAGTGATTTTGT | 52.1 | 11 |
| hsa-miR-143-3p | UGAGAUGAAGCACUGUAGCUC | TGAGATGAAGCACTGTAGC | 51.9 | 12 |
| hsa-miR-145-5p | GUCCAGUUUUCCCAGGAAUCCCU | GTCCAGTTTTCCCAGGAATCC | 55.7 | 13 |
| hsa-miR-21-5p | UAGCUUAUCAGACUGAUGUUGA | TAGCTTATCAGACTGATGTT | 47.9 | 14 |
| hsa-miR-1908-5p | CGGCGGGGACGGCGAUUGGUC | CGGCGGGGACGGCGATTGG | 66.9 | 15 |
| hsa-miR-1260b | AUCCCACCACUGCCACCAU | ATCCCACCACTGCCACC | 57.9 | 16 |

Tm: (Melting temperature: temperature at which the primer/mold duplex is in monocatenary form)

The forward primers used were specifically designed for the present essay, and in some cases are shorter than their corresponding miRNA. The design was produced in order to eliminate possible secondary structures (hairpin loops) which limit their use as primer, and adjusting their Tm so as to allow the joint analysis of the eight miRNAs and/or to keep the possible hairpins far enough away from the Tm to avoid their formation during the annealing and amplification phase. This ensured that the detected miRNAs were only mature miRNAs. If the precursors were also detected, two Tm of the amplified PCR product would be observed, but this was never observed.

Real-time amplificacion was done in a LightCycler® 480 Real-Time PCR System (Roche, Suiza) thermal cycler, under standard amplification conditions that included a step of activation of the hotstart polymerase for 15 minutes at 94° C. followed by 45 cycles consisting of 3 steps: denaturing for 15 seconds at 95° C., hybridization for 30 seconds at 55° C. and extension for 30 seconds at 70° C. The relative quantification of the amplified products was done using the amplification levels of a nuclear RNA, specifically the snRNA U6, of each sample. The specific primer for amplification of the U6 used is a component of the kit.

Figure 3:
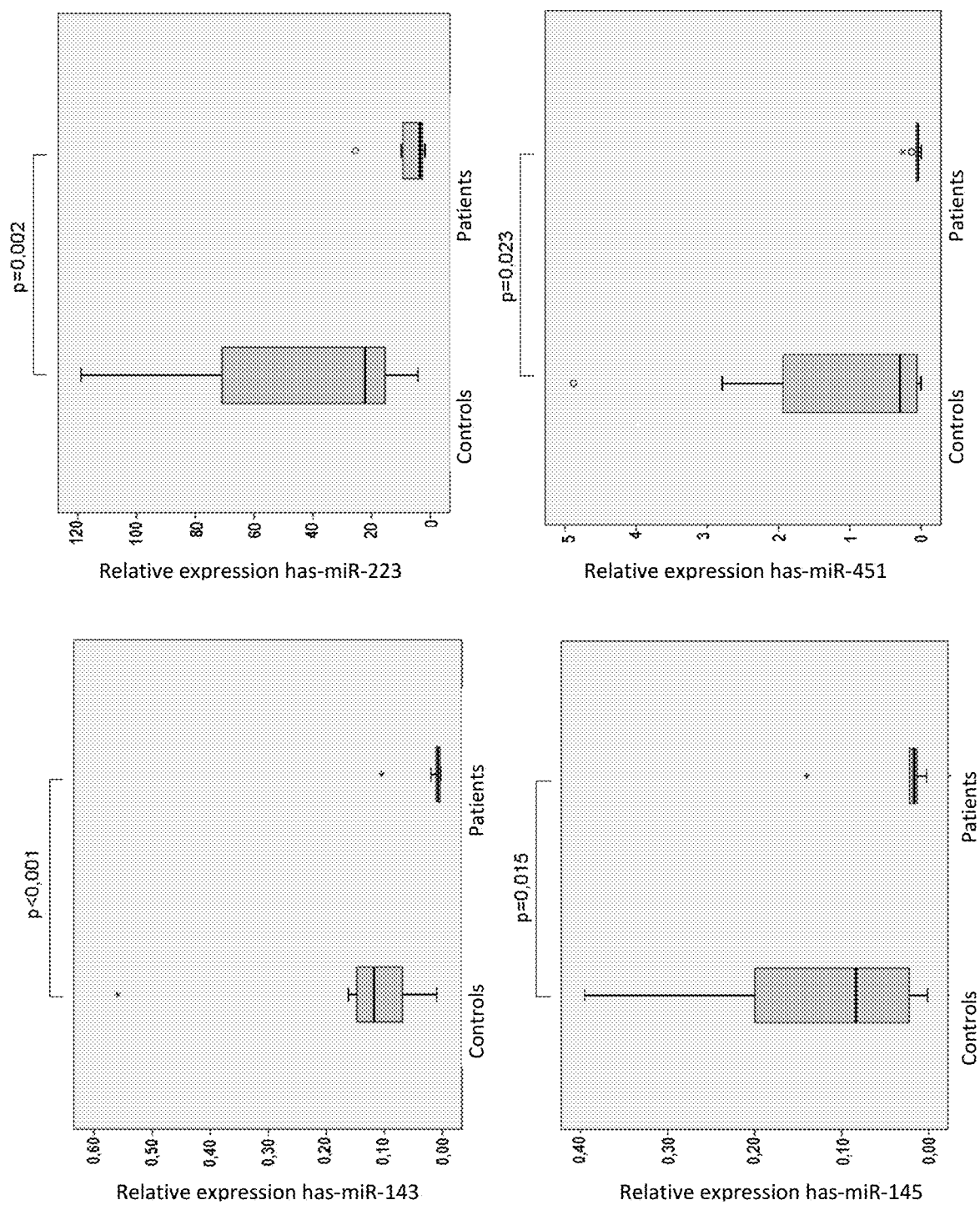
FIG. 3. Box plots corresponding to the amplification of miRNAs by standardized qPCR in fibromyalgia patients ("Patients") and control subjects ("Controls"). The values are considered significant if $p<0.05$ (Mann-Whitney U test), which is indicated by an asterisk in each graph. The microRNA to which each graph corresponds is indicated in ordinates, indicating only the number thereof and not the possible precisions for tissue of expression or branch of the pre-miRNA from which it results (hsa-miR-143: hsa-miR-143-3p, hsa-miR-145: hsa-miR-145-5p, hsa-miR-223: hsa-miR-223-3p, hsa-miR-451: hsa-miR-451a, hsa-miR-338: hsa-miR-338-3p, hsa-miR-1908: hsa-miR-1908-5p, hsa-miR-1260: hsa-miR-1260b, hsa-miR-21: hsa-miR-21-5p).
Figure 3:
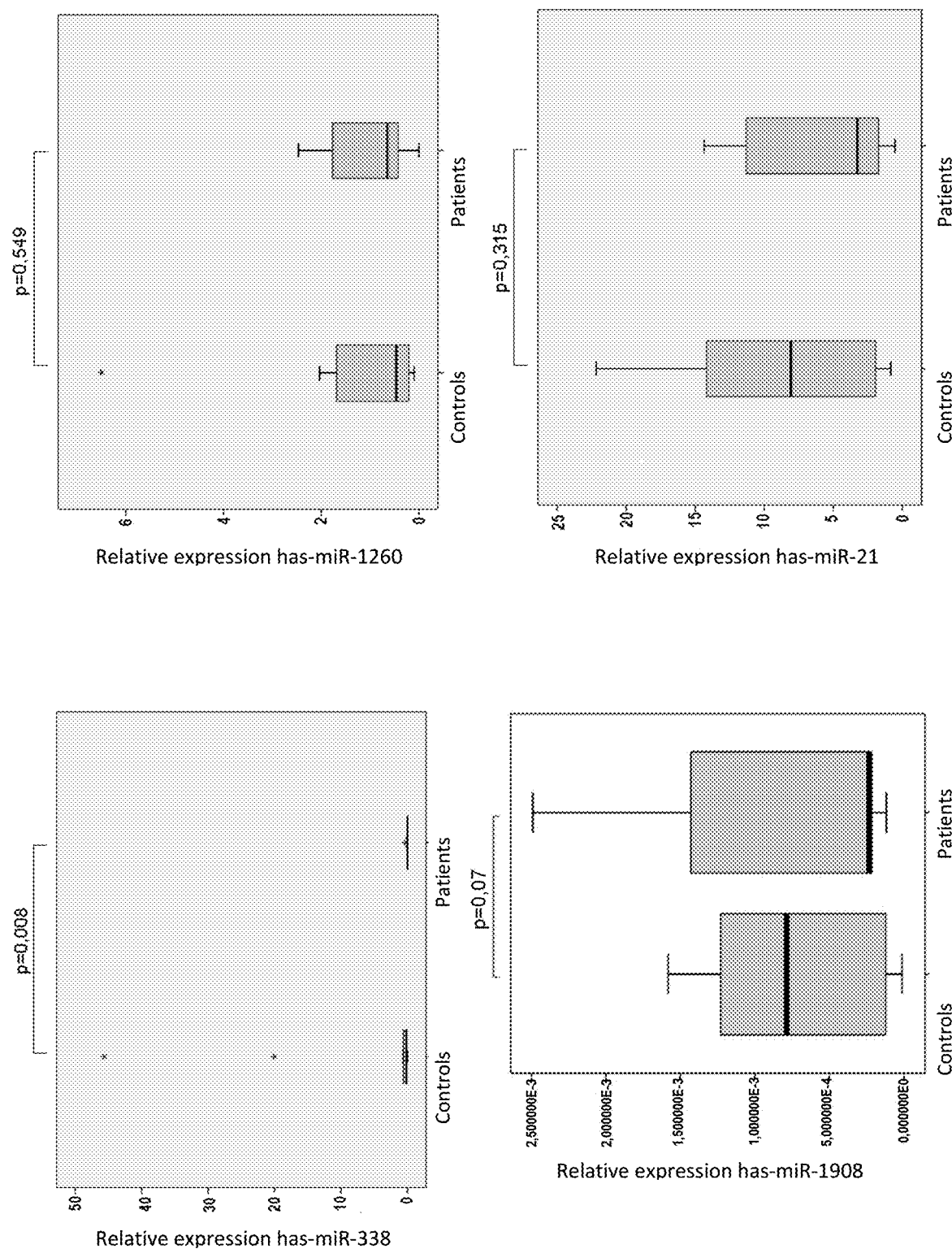

The results obtained are indicated below in Table 9, and have been represented in FIG. 3. It can be seen in this figure that the miRNAs initially selected as possible fibromyalgia biomarkers show significant variations ($p<0.05$), while the three markers selected as controls (hsa-miR-21-5p, hsa-miR-1908-5p, and hsa-miR-1260b) show no significant variations ($p>0.05$).

TABLE 9

Determination of the relative expression of miRNAs in patients (FM) vs Controles (C) by means of Q-PCR. The results are expressed as medians (−delta Ct), ΔΔCt, change factor (fold change: $2^{\Delta\Delta Ct}$). The changes are considered significant if $p \leq 0.05$.

| miRNA | FM Median (−delta Ct) | C Median (−delta Ct) | ΔΔCt | Change factor ($2^{\Delta\Delta Ct}$) | P Value |
|---|---|---|---|---|---|
| hsa-miR-223-3p | 22.1 | 17.8 | 4.3 | 19.7 | 0.00 |
| hsa-miR-451a | 30.0 | 23.8 | 6.2 | 73.5 | 0.02 |
| hsa-miR-338-3p | 30.7 | 24.1 | 6.6 | 97.0 | 0.00 |
| hsa-miR-145-5p | 31.0 | 25.4 | 5.6 | 48.5 | 0.01 |
| hsa-miR-143-3p | 31.5 | 25.4 | 6.1 | 68.5 | 0.00 |
| hsa-miR-21-5p | 23.1 | 20.1 | 3.0 | 8.0 | 0.31 |
| hsa-miR-1908-5p | 36.4 | 32.9 | 3.5 | 11.3 | 0.07 |
| hsa-miR1260b | 25.8 | 22.9 | 2.9 | 7.46 | 0.54 |

The results from the table above confirm, by an alternative technique (quantitative PCR), that the levels of the miRNAs hsa-miR-143-3p, hsa-miR-145-5p, hsa-miR-223-3p, hsa-miR-338-3p and hsa-miR-451a are significantly reduced ($p<0.05$) in FM patients, while the levels of the hsa-miR-21-5p, hsa-miR-1260b and hsa-miR-1908-5p show no significant differences between groups.

Therefore, the selected microRNAs are suitable for basing a method for diagnosing fibromyalgia patients.

Example 3: Association Between Levels of miRNAs and Fibromyalgia Symptoms

In order to determine if the differences observed between the levels of expression of the miRNAs hsa-miR-143-3p (mir-143), hsa-miR-145-5p (miR-145), hsa-miR-223-3p (miR-223), hsa-miR-338-3p (miR-338) and hsa-miR-451a (miR-451) are associated with the symptomatic severity of the patients, their correlation was evaluated with the FIQ score (as indicator of the impact of the disease) and the levels of mental fatigue (MF). In both cases, the greater the value the greater the impact of the symptomatology in the life of the patient. According to the results obtained, the patient will be considered to present with a low level of mental fatigue when presenting with a level of 10 or less than 10, evaluated according to the aforementioned Multi-dimensional Fatigue Questionnaire.

Figure 4:
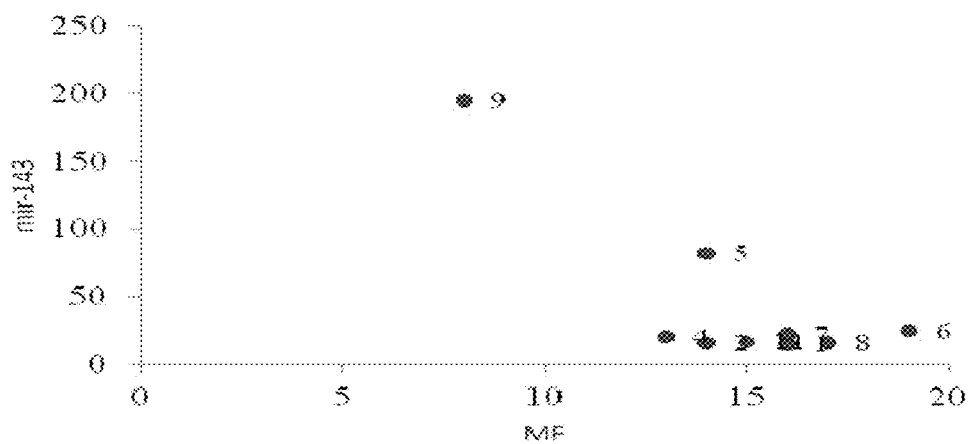
FIG. 4. Graphs that represent the correlation between the level of mental fatigue (MF, represented on the abscissa axis) and the levels of expression of the microRNAs miR-143 (hsa-miR-143-3p), miR-145 (hsa-miR-145-5p), miR-223 (hsa-miR-223-3p), miR-451 (hsa-miR-451a), miR-338 (hsa-miR-338-3p), miR-21 (hsa-miR-21-5p), miR-1260 (hsa-miR-1260b).
Figure 4:
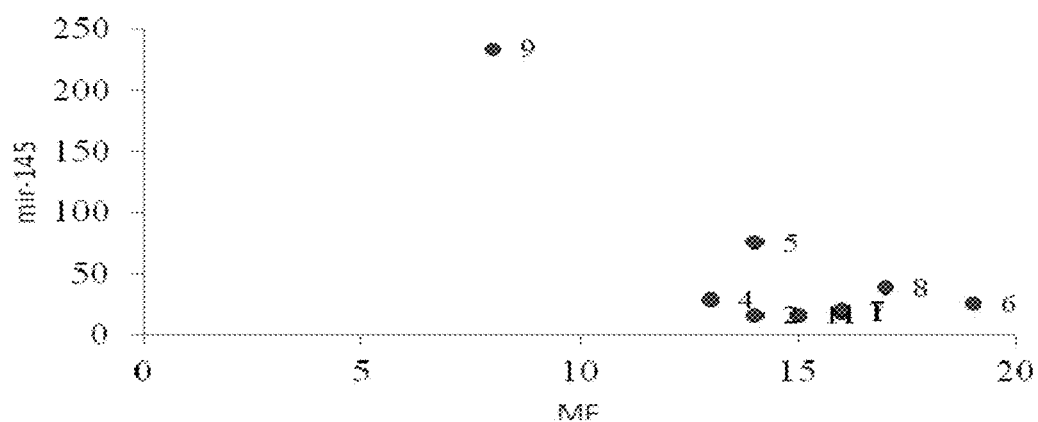
Figure 4:
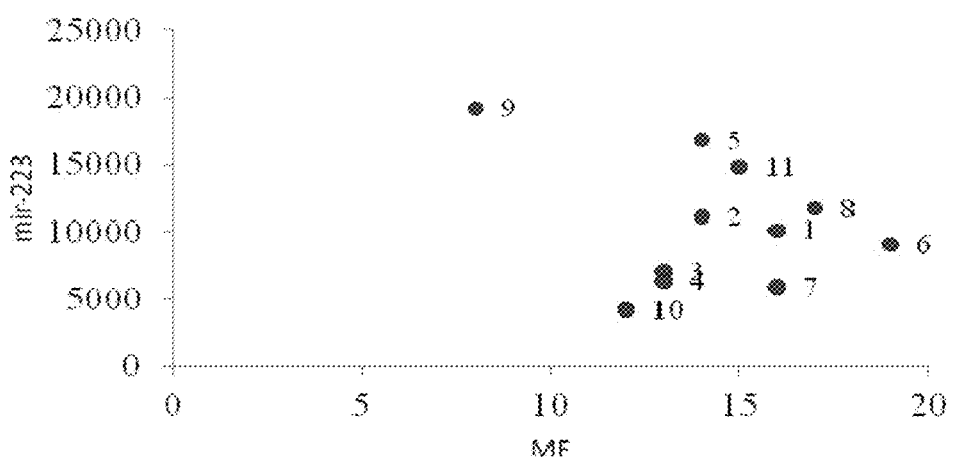
Figure 4:
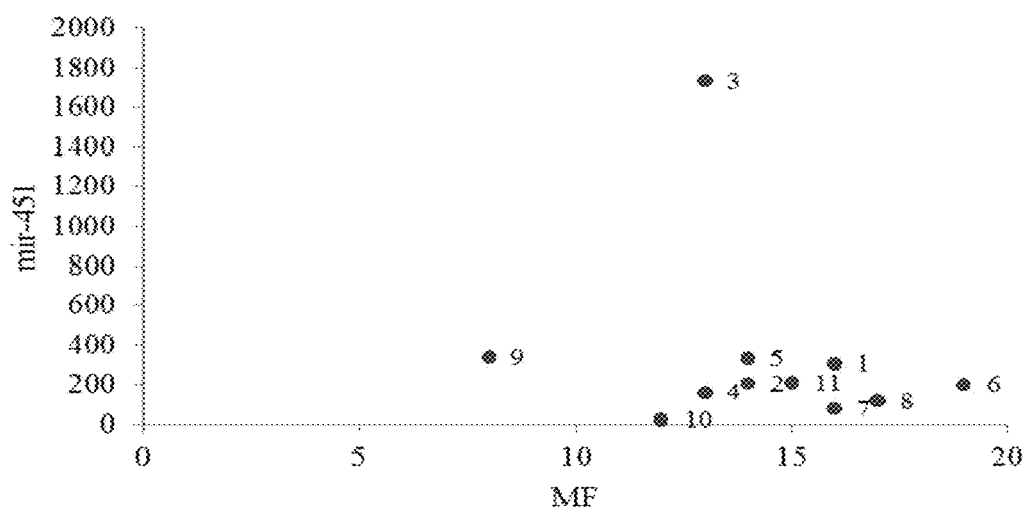
Figure 4:
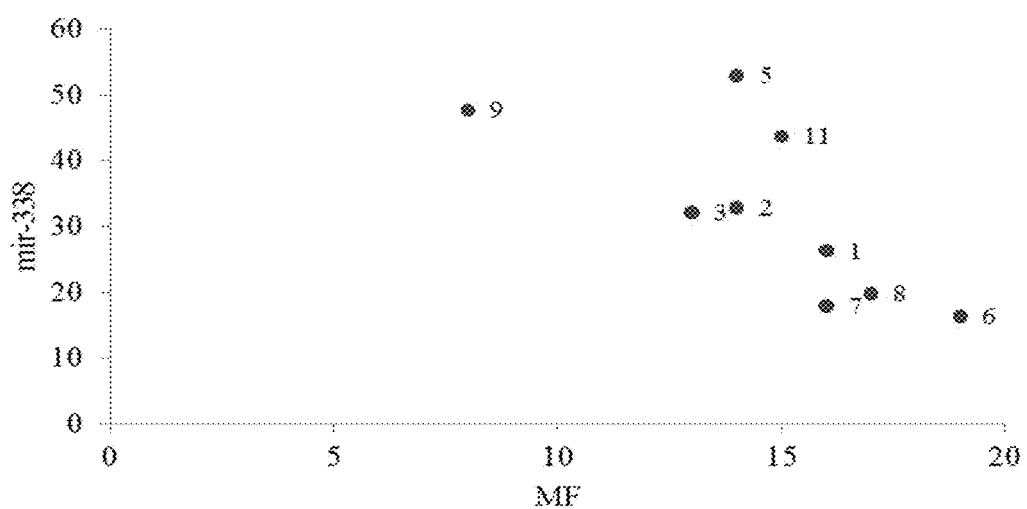
Figure 4:
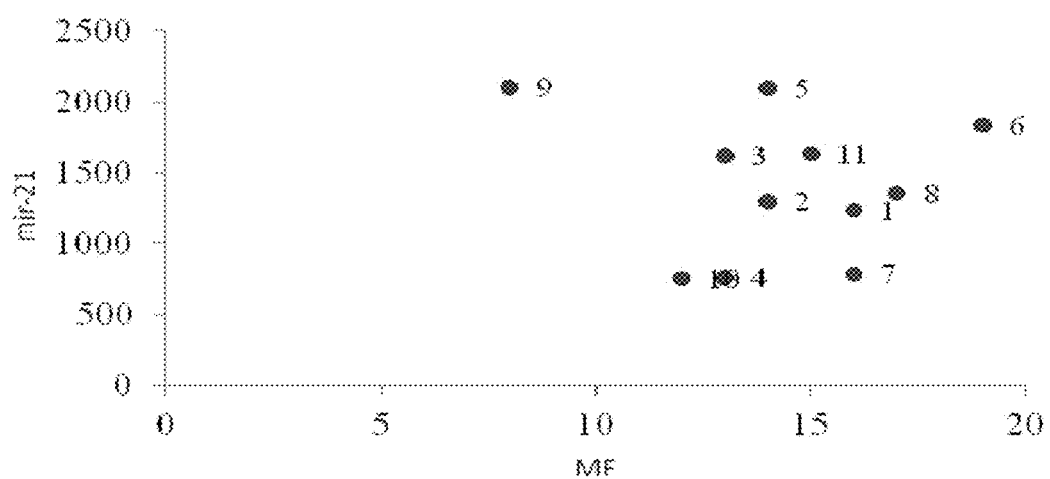
Figure 4:
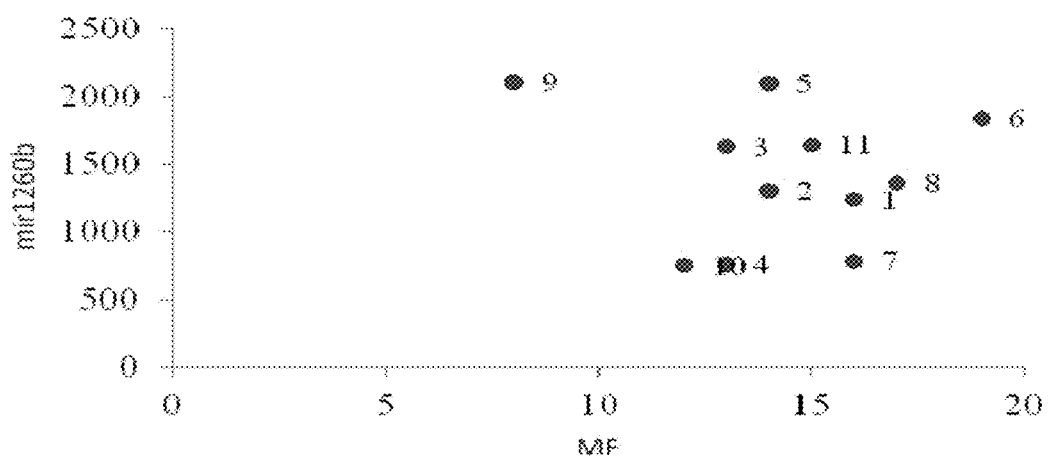

The results obtained from the statistical analysis of correlation of each of the inhibited miRNAs and the scores from the FIQ and MFI scores are shown in Table 10 below. In FIG. 4 a representation can be observed of the correlation between each of the miRNAs and mental fatigue (MF).

TABLE 10

Relation of miRNAs associated with FM with cardinal symptoms of the disease

| Spearman | Column 1 | miR-143 | miR-145 | miR-223 | miR-338 | miR-451 |
|---|---|---|---|---|---|---|
| FIQ | n | 9 | 9 | 11 | 9 | 11 |
|  | rs | −0.19 | 0.14 | 0.03 | 0.10 | −0.33 |
|  | t-stat | 0.41 | 0.35 | 0.33 | 0.36 | 0.38 |
|  | P Value | 0.693 | 0.737 | 0.750 | 0.730 | 0.710 |
| MF | n | 9 | 9 | 11 | 9 | 11 |
|  | rs | −0.38 | −0.37 | 0.01 | −0.76 | −0.58 |
|  | t-stat | 0.44 | 0.44 | 0.33 | 0.50 | 0.42 |
|  | P Value | 0.671 | 0.671 | 0.748 | 0.631 | 0.685 | n: Number of individuals
rs: Spearman rho of the relative abundance of miRNAs compared to symptomatic severity
t-stat:: "two-tailed signficance"

Although in none of the cases could a statistically significant correlation be seen, in the observation of FIG. 4 and in the analysis of the data of Tables 6 and 7, especially the former, the fact is clear that patient 9, with a lower mental fatigue index, is several levels closer to those of the control miRNAs, especially in three of the miRNAs selected as markers (hsa-miR-143-3p, hsa-miR-145-5p and hsa-miR-223-3p), and does not show marked differences compared to the remaining values of the group of patients for the control miRNAs (hsa-miR-21-5p and hsa-miR-1260b).

Therefore, it is proposed that the diagnostic method include an additional step in which it is determined that a patient, although suffering from fibromyalgia, has a low level of mental fatigue when the five miRNAs of the group miR-223, miR-451, miR-338, miR-143 and miR-145 (or alternatively four, disregarding miR-143 or miR-145) and only the levels of miR-451 and miR-338 are less than their corresponding reference values; preferably, low level of mental fatigue will only be diagnosed when the negative controls miR-21, miR-1260b and miR-1908 have also been analyzed and at least two of them do not have levels with values lower than their corresponding reference values; more preferably still, the criterion will also be included that the third microRNA of the group of negative controls will also not have a level with a value that can be considered less than its corresponding reference value or that the decrease compared to the reference value is less than 4, or preferably less than 3.

---

The invention claimed is:

1. A method for diagnosing whether an individual suffers from the disease of fibromyalgia, which comprises the steps of:
    a) measuring the level of miR-223, miR-451, or a combination thereof in a peripheral blood sample taken from the individual;
    b) deciding that the individual suffers from disease of fibromyalgia if the level of at least one of the measured miRNAs has a value lower than a corresponding reference value, wherein for each miRNA, its corresponding reference value is the average value of the level of expression of said miRNA in healthy individuals; and
    c) treating the individual for fibromyalgia.

2. The method according to claim 1, further comprising measuring the level of miR-338, miR-143, or miR-145, further comprising deciding that the individual suffers from the disease of fibromyalgia if the level of miR-338, miR-143, miR-145, or a combination thereof has a value lower than the corresponding reference value.

3. The method according to claim 1, further comprising measuring the level of miR-338, miR-143, and miR-145.

4. The method according to claim 1, further comprising measuring the level of miR-21, miR-1908, miR-1260b, or a combination thereof, further comprising deciding that the patient suffers from the disease of fibromyalgia if the level of miR-21, miR-1260b, or miR-1908, or a combination thereof does not have a value lower than the corresponding reference value.

5. The method according to claim 1, further comprising measuring the level of all three of miR-21, miR-1908, miR-1260b, wherein it is decided that the patient suffers from the disease of fibromyalgia if the level of all three miRNAs from the group miR-21, miR-1260b and miR-1908 does not have a value lower than the corresponding reference value.

6. The method according to claim 1, wherein the miRNA level has a value lower than the corresponding reference value when the value is one half of the reference value or less.

7. The method according to claim 1, wherein the miRNA level measurement is made on peripheral blood mononuclear cells obtained from the patient.

8. The method according to claim 1, wherein the miRNA level measurement is detected by quantitative PCR (qPCR).

9. The method according to claim 1, further comprising determining that a patient who has been diagnosed with fibromyalgia has a low level of mental fatigue when, from the group of miR-223, miR-451, miR-338, miR-143 and miR-145, only the levels of the microRNAs miR-451 and miR-338 have a lower level than their corresponding reference values.

10. The method according to claim 1, wherein it is determined that a patient who has been diagnosed with fibromyalgia has a low level of mental fatigue when, additionally, the negative controls miR-21, miR-1260b and miR-1908 have been analyzed and at least two thereof do not have levels with values lower than their respective reference values.

11. The method according to claim 1, wherein the miRNA level measurement is detected using a microchip.

12. The method according to claim 1, wherein the miRNA level measurement is detected by quantitative PCR with prior retrotranscription, and the forward primers of the quantitative PCR are selected from the group of: SEQ ID NO:9 (for hsa-miR-223-3p) and SEQ ID NO:10 (for hsa-miR-451a).

13. The method according to claim 2, wherein the miRNA level measurement is detected by quantitative PCR with prior retrotranscription, and the forward primers of the quantitative PCR are selected from the group of: SEQ ID NO:11 (for hsa-miR-338-3p), SEQ ID NO:12 (for hsa-miR-143-3p), SEQ ID NO:13 (for hsa-miR-145-5p).

14. The method according to claim 4, wherein the miRNA level measurement is detected by quantitative PCR with prior retrotranscription, and the forward primers of the quantitative PCR are selected from the group of: SEQ ID NO:14 (for hsa-miR-21-5p), SEQ ID NO:15 (hsa-miR-1908-5p), SEQ ID NO:16 (for hsa-miR-1260b).

* * * * *

SEQUENCE LISTING

```
<160> NUMBER OF SEQ ID NOS: 16

<210> SEQ ID NO 1
<211> LENGTH: 22
<212> TYPE: RNA
<213> ORGANISM: Homo sapiens
<220> FEATURE:
<223> OTHER INFORMATION: Mature hsa-miR-223-3p sequence

<400> SEQUENCE: 1
ugucaguuug ucaaauaccc ca                                        22

<210> SEQ ID NO 2
<211> LENGTH: 22
<212> TYPE: RNA
<213> ORGANISM: Homo sapiens
<220> FEATURE:
<223> OTHER INFORMATION: Mature hsa-miR-451a sequence

<400> SEQUENCE: 2
aaaccguuac cauuacugag uu                                        22

<210> SEQ ID NO 3
<211> LENGTH: 22
<212> TYPE: RNA
<213> ORGANISM: Homo sapiens
<220> FEATURE:
<223> OTHER INFORMATION: Mature hsa-miR-338-3p sequence

<400> SEQUENCE: 3
uccagcauca gugauuuugu ug                                        22

<210> SEQ ID NO 4
<211> LENGTH: 21
<212> TYPE: RNA
<213> ORGANISM: Homo sapiens
<220> FEATURE:
<223> OTHER INFORMATION: Mature hsa-miR-143-3p sequence

<400> SEQUENCE: 4
ugagaugaag cacuguagcu c                                         21
```

<210> SEQ ID NO 5
<211> LENGTH: 23
<212> TYPE: RNA
<213> ORGANISM: Homo sapiens
<220> FEATURE:
<223> OTHER INFORMATION: Mature hsa-miR-145-5p sequence

<400> SEQUENCE: 5
guccaguuuu cccaggaauc ccu                                         23

<210> SEQ ID NO 6
<211> LENGTH: 22
<212> TYPE: RNA
<213> ORGANISM: Homo sapiens
<220> FEATURE:
<223> OTHER INFORMATION: Mature hsa-miR21-5p sequence

<400> SEQUENCE: 6
uagcuuauca gacugauguu ga                                          22

<210> SEQ ID NO 7
<211> LENGTH: 21
<212> TYPE: RNA
<213> ORGANISM: Homo sapiens
<220> FEATURE:
<223> OTHER INFORMATION: Mature hsa-miR1908-5p sequence

<400> SEQUENCE: 7
cggcggggac ggcgauuggu c                                           21

<210> SEQ ID NO 8
<211> LENGTH: 19
<212> TYPE: RNA
<213> ORGANISM: Homo sapiens
<220> FEATURE:
<223> OTHER INFORMATION: Mature hsa-miR-1260b sequence

<400> SEQUENCE: 8
aucccaccac ugccaccau                                              19

<210> SEQ ID NO 9
<211> LENGTH: 20
<212> TYPE: DNA
<213> ORGANISM: Artificial sequence
<220> FEATURE:
<223> OTHER INFORMATION: Forward primer for hsa-miR-223-3p cDNA
      amplification

<400> SEQUENCE: 9
tgtcagtttg tcaaataccc                                             20

<210> SEQ ID NO 10
<211> LENGTH: 20
<212> TYPE: DNA
<213> ORGANISM: Artificial sequence
<220> FEATURE:
<223> OTHER INFORMATION: Forward primer for hsa-miR-451a cDNA
      amplification

<400> SEQUENCE: 10
aaaccgttac cattactgag                                             20

<210> SEQ ID NO 11
<211> LENGTH: 20
<212> TYPE: DNA
<213> ORGANISM: Artificial sequence

```
<220> FEATURE:
<223> OTHER INFORMATION: Forward primer for hsa-miR-338-3p cDNA
      amplification

<400> SEQUENCE: 11
tccagcatca gtgattttgt                                                    20

<210> SEQ ID NO 12
<211> LENGTH: 19
<212> TYPE: DNA
<213> ORGANISM: Artificial sequence
<220> FEATURE:
<223> OTHER INFORMATION: Forward primer for hsa-miR143-3p cDNA
      amplification

<400> SEQUENCE: 12
tgagatgaag cactgtagc                                                     19

<210> SEQ ID NO 13
<211> LENGTH: 21
<212> TYPE: DNA
<213> ORGANISM: Artificial sequence
<220> FEATURE:
<223> OTHER INFORMATION: Forward primer for hsa-miR-145-5p cDNA
      amplification

<400> SEQUENCE: 13
gtccagtttt cccaggaatc c                                                  21

<210> SEQ ID NO 14
<211> LENGTH: 20
<212> TYPE: DNA
<213> ORGANISM: Artificial sequence
<220> FEATURE:
<223> OTHER INFORMATION: Forward primer for hsa-miR-21-5p cDNA
      amplification

<400> SEQUENCE: 14
tagcttatca gactgatgtt                                                    20

<210> SEQ ID NO 15
<211> LENGTH: 18
<212> TYPE: DNA
<213> ORGANISM: Artificial sequence
<220> FEATURE:
<223> OTHER INFORMATION: Forward primer for hsa-miR-1908-5p cDNA
      amplification

<400> SEQUENCE: 15
cggcggggac ggcgattg                                                      18

<210> SEQ ID NO 16
<211> LENGTH: 17
<212> TYPE: DNA
<213> ORGANISM: Artificial sequence
<220> FEATURE:
<223> OTHER INFORMATION: Forward primer for hsa-miR-1260b cDNA
      amplification

<400> SEQUENCE: 16
atcccaccac tgccacc                                                       17
```